US012747204B2

(12) United States Patent
Migliorini et al.

(10) Patent No.: US 12,747,204 B2
(45) Date of Patent: Sep. 29, 2026

(54) PROCESS FOR THE PREPARATION OF CYSTEAMINE BITARTRATE AND PRODUCT SO OBTAINED

(71) Applicant: Recordati Industria Chimica e Farmaceutica S.p.A., Milan (IT)

(72) Inventors: Antonella Migliorini, Rome (IT); Francesco Yafteh Mihan, Aprilia (IT); Franca Segnalini, Latina (IT); Angela Tuozzi, Latina (IT)

(73) Assignee: Recordati Industria Chimica e Farmaceutica S.p.A., Milan (IT)

( * ) Notice: Subject to any disclaimer, the term of this patent is extended or adjusted under 35 U.S.C. 154(b) by 950 days.

(21) Appl. No.: 18/087,969

(22) Filed: Dec. 23, 2022

(65) Prior Publication Data

US 2023/0202975 A1 Jun. 29, 2023

Related U.S. Application Data

(60) Provisional application No. 63/266,021, filed on Dec. 27, 2021.

(51) Int. Cl.
*C07C 319/06* (2006.01)
*C07C 59/255* (2006.01)
*C07C 323/25* (2006.01)

(52) U.S. Cl.
CPC .......... *C07C 319/06* (2013.01); *C07C 59/255* (2013.01); *C07C 323/25* (2013.01); *C07B 2200/13* (2013.01)

(58) Field of Classification Search
CPC . C07B 2200/13; C07C 319/06; C07C 319/28; C07C 323/25; C07C 51/43; C07C 59/255; C07D 277/04
See application file for complete search history.

(56) References Cited

U.S. PATENT DOCUMENTS

| | | | | |
|---|---|---|---|---|
| 4,011,233 | A | 3/1977 | Dubs et al. | |
| 5,017,725 | A | 5/1991 | Hohmann et al. | |
| 10,221,132 | B2 | 3/2019 | Baratella et al. | |
| 10,251,850 | B2 | 4/2019 | Chaudhari et al. | |
| 2018/0193292 | A1* | 7/2018 | Chaudhari | A61K 31/095 |

FOREIGN PATENT DOCUMENTS

| | | | |
|---|---|---|---|
| CN | 106146427 | * | 11/2016 |
| CN | 106146427 | A | 11/2016 |
| EP | 0 054 409 | A1 | 6/1982 |
| EP | 3 842 418 | A1 | 6/2021 |
| GB | 2 054 573 | A | 2/1981 |
| IN | 202041000697 | * | 7/2021 |

OTHER PUBLICATIONS

CN106146427 translated (Year: 2016).*
Office Action mailing date of Jul. 13, 2026, in corresponding Indian Patent Application No. 202447048264.
Srinivasan Thirumalai Rajan, “An improved process for the preparation of Cysteamine Bitartrate”, Technical Disclosure Commons, Jan. 2021, pp. 1-17.
Tzou-Chi Huang et al., “Mechanistic Studies on Thiazolidine Formation in Aldehyde/Cysteamine Model Systems”, J. Agric. Food Chem. 1998, 46, pp. 224-227.
Ying Fu, et al., “Design, Synthesis, Safener Activity, and Molecular Docking of Novel N-Substituted Thiazide/Thiazole Derivatives”, Journal of Heterocyclic Chemistry, vol. 000, 2018, 8 pages.
Fanny Danton et al., “PIDA/$I_2$-Mediated Domino Approach for Pyrrolo[1,4]Thiazines and 1,4-Thiazines via a ‘One-pot’ Morin Rearrangement of N,S-Acetals”, Chemistry—A European Journal, 10.1002/chem.201901111, 2019, 8 pages.
Amina Benylles et al., “Three salts from the reactions of cysteamine and cystamine with L-(+) tartaric acid”, Crystallography Journals, Acta Cryst. (2013). C69, 658-664, (215-222).
Akio Yasuhara et al., “Determination of Physical and Spectral Data on Thiazolidines for Trace Aldehyde Analysis”, Agric. Biol. Chem., 53 (8), 1989, pp. 2273-2274.

* cited by examiner

*Primary Examiner* — Andrew D Kosar
*Assistant Examiner* — Blaine G Doletski
(74) *Attorney, Agent, or Firm* — Oblon, McClelland, Maier & Neustadt, L.L.P.

(57) ABSTRACT

The present invention relates to a new, enhanced process for the manufacture of Cysteamine Bitartrate (I) and of its key intermediate thiazolidine (II).

Furthermore, it relates to a new processes for the manufacture of crystalline anhydrous Cysteamine Bitartrate (polymorph L2) and monohydrate Cysteamine Bitartrate (polymorph L1). The crystalline anhydrous Cysteamine Bitartrate (polymorph L2) so obtained is characterized by particularly fine particle size and good appearance.

24 Claims, 9 Drawing Sheets

PROCESS FOR THE PREPARATION OF CYSTEAMINE BITARTRATE AND PRODUCT SO OBTAINED

FIELD OF INVENTION

The present invention refers to an improved process for the preparation of Cysteamine Bitartrate and to the crystalline anhydrous stable polymorph powder so obtained.

BACKGROUND

Cysteamine Bitartrate of formula (I)

(I)

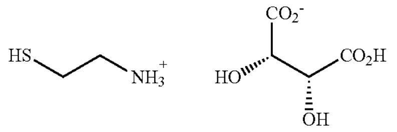

(M. W. 227.24, $C_6H_{13}NO_6S$) is a cystine-depleting agent, which lowers the cystine content of cells in patients with cystinosis, an inherited defect of lysosomal transport, indicated for the management of nephropathic cystinosis in children and adults.

According to the literature and to Applicant experience, it is not practicable preparing Cysteamine Bitartrate starting from Cysteamine Hydrochloride, readily available on the market, by simple exchange of Chloride-Bitartrate counterions but it is necessary to pass through Cysteamine free-base.

Cysteamine Bitartrate is thus typically prepared by salification with L (+)-tartaric acid of Cysteamine free base released from Cysteamine salts by basic treatment, as illustrated in Scheme 1 below starting from the hydrochloride:

Scheme 1

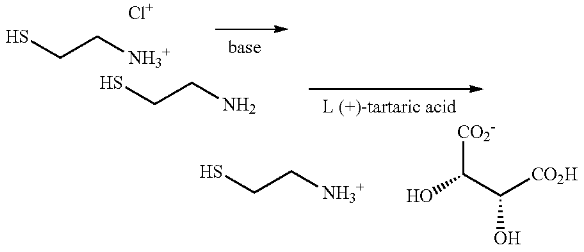

(I)

For instance, U.S. Ser. No. 10/251,850 describes the preparation of Cysteamine Bitartrate starting from Cysteamine free-base or its salts, in particular from Cysteamine Hydrochloride. Furthermore, this document describes the preparation of Cysteamine Bitartrate crystalline forms L1 and L2, by crystallization from methanol at −5/−25° C. and −25/−30° C. respectively, and their analytical characterization.

U.S. Ser. No. 10/221,132 discloses the manufacturing of Cysteamine Bitartrate (I) starting from Cysteamine Hydrochloride, by releasing Cysteamine free-base with tributylamine followed by salification with L (+)-tartaric acid (Ex. 5). Cysteamine Bitartrate is then crystallized from an admixture of methanol/2-propanol (1:1).

Acta Cyst. (2013), 658-664, under the experimental section, describes the preparation and crystallization of Cysteamine Bitartrate monohydrate by reaction of Cysteamine free base and L(+)-tartaric acid in 1:1 ratio in ethanol.

One critical issue in the above syntheses of Cysteamine Bitartrate is to obtain and maintain high product purity, as Cysteamine salts, especially in basic environment or in the presence of metal ions, are unstable and easily oxidized to the disulfide Cystamine (see for instance Journal of Pharmaceutical Analysis 2020, 10 499-516, par. 3). Cystamine, in addition to not being pharmacologically active, is difficult to eliminate by extraction, crystallization or distillation because its molecular weight and acid-base properties are similar to those of Cysteamine.

In this respect, EP3842418A1 discloses a method for the purification of Cysteamine or a salt thereof from polisolfurica impurities, in particular from Cystamine, by treatment with dithiothreitol. Example 2 describes the purification of crude Cysteamine Bitartrate, containing 2.5% Cystamine, through dissolution in water and precipitation by addition of an anti-solvent (2-propanol) to the aqueous solution. The resulting solid still includes 0.19% Cystamine (HPLC).

Other processes for the synthesis of Cysteamine use 2-substituted thiazolidines as a convenient, purificable, stable Cysteamine precursor to be opened under acidic conditions e.g. with a hydrohalogenic acid HX, as depicted in the Scheme 2 below:

Scheme 2

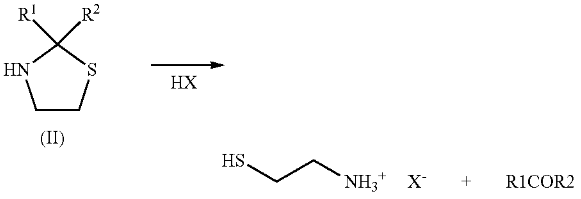

For instance, GB2054573A discloses the reaction of 2, 2-disubstituted thiazolidines with mineral acids such as HCl or HBr in the presence of water to provide the corresponding Cysteamine salts.

U.S. Pat. No. 5,017,725 describes the acid hydrolysis of the intermediate 2, 2-disubstituted thiazolidine by reaction with ammonium or a metal hydrogen sulphide with the addition of a medium to strong acid, preferably hydrochloric acid, to provide Cysteamine Hydrochloride.

EP54409A1 is directed to the preparation of 2-monosubstituted-thiazolidines such as 2-phenylthiazolidine and to their use as intermediates in several manufacturing processes, including the preparation of Cysteamine Hydrochloride by ring opening with hydrochloric acid or with organic acids such as acetic acid or oxalic acid, to be then converted into the hydrochloride.

In turn, 2-substituted thiazolidines can be prepared from precursors such as, for instance, an ethanolamine derivative, an aldehyde and a sulfur donor as described in EP54409A1 or possibly from Cysteamine salts and ketones, as described in the following documents under the reported conditions:

- CN106146427A, starting from Cysteamine Hydrochloride by reaction with acetone in cyclohexane at a pH of about 7 (see Ex. 1 dropwise soda to neutrality);
- Agric. Biol. Chem. (1989), vol. 53, 8, 2273-2274, starting from an aqueous solution of Cysteamine Hydrochloride brought to pH of 6.2 by addition of diluted soda and then reacted with an aqueous methanol solution of the chosen aldehyde or ketone;

U.S. Pat. No. 4,011,233 starting from Cysteamine free-base by reaction with aldehydes or ketones;

J. Het. Chem. (2019), vol. 56, 1, 180-187 and Chem. A Eur. J. (2019), vol. 25, 24, 6113-6118 from Cysteamine HCl in methanol or in toluene under acidic catalysis;

J. Agric. and food chemistry (1998), vol. 46, 1, 224-227, from Cysteamine and aldehydes in a phosphate buffer preferably at pH of 7.2, discouraging higher pH, such as pH of 10.3 of a carbonate buffer, because of formation of significant amount of thiazoline by-product (see page 226, right column, last 5 lines of the 1st paragraph).

In conclusion, according to the above state of the art, the preparation of Cysteamine Bitartrate starting from viable and cheap raw Cysteamine salts through the intermediate thiazolidine is quite long and with overall scarce yields, as it comprises altogether at least the following steps:

Preparation of an intermediate thiazolidine (II) from e.g. raw Cysteamine or a salt thereof by reaction with an aldehyde or a ketone, under neutral or slightly acidic conditions followed by purification;

ring opening by hydrolysis of the thiazolidine, typically with a hydrogen halide acid, with formation and isolation of the corresponding Cysteamine salt;

Release of Cysteamine free base from the salt by basic treatment, and salification of Cysteamine free base with L (+)-tartaric acid to provide Cysteamine Bitartrate (I), as summarized in the Scheme 3 below:

Scheme 3

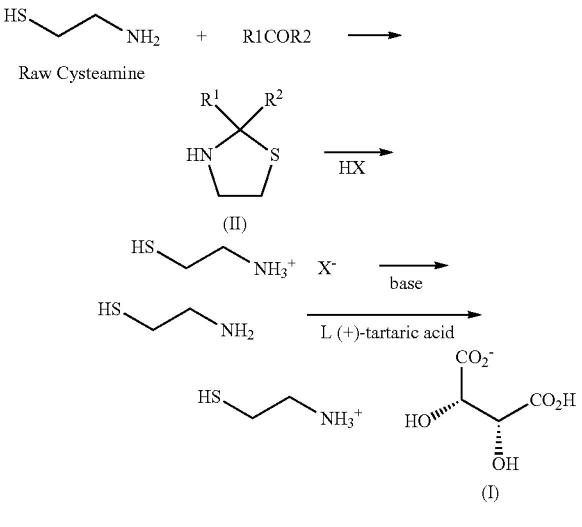

A recently described more straightforward preparation is based on the direct opening of the intermediate thiazolidine with L(+)-tartaric acid to provide Cysteamine Bitartrate in fewer steps.

In this respect, the technical disclosure entitled "*An improved process for the preparation of Cysteamine Bitartrate*" (Technical Disclosure Commons, Srinivasan Tirumala Rajang, MSN Laboratories Private Limited, R&D Centre, January 2021) and the related patent application IN202041000697A, describe the preparation of Cysteamine Bitartrate by direct opening of substituted thiazolidines, in particular of 2-methyl-2-ethyl-thiazolidine (Ex. 8-9), with L (+)-tartaric acid.

However, these processes show some drawbacks especially for a large-scale manufacture. In fact, the crude 2,2-disubstituted thiazolidine—prepared from ethanolamine through formation of 2-aminoethyl hydrogensulfate and subsequent reaction with a ketone under acid catalysis—comprises undesired by-products that interfere in the manufacture so that the overall process yields and purity of the crude Cysteamine Bitartrate are not completely satisfactory, as confirmed in the present experimental section.

These documents (see Ex. 6 and Ex. 10) also describe the preparation of a Cysteamine Bitartrate form M by addition of the anti-solvent 2-propanol to the aqueous solution of the crude Cysteamine Bitartrate.

The addition of the anti-solvent to the aqueous solution of Cysteamine Bitartrate is herein referred as "direct" addition. According to the Applicant assessments (see the present experimental part, Example 10 and the following comments), the final crystalline powder obtained by direct addition can be endowed with non-optimal flowability properties.

SUMMARY OF THE INVENTION

The Applicant, with the aim to improve the known processes for manufacturing Cysteamine Bitartrate, has envisaged a particularly advantageous route of synthesis that starting from an even raw Cysteamine salt in fewer, simple steps, with little intermediate work up and purifications, provides Cysteamine Bitartrate in high yield, purity and, after crystallization under new conditions, improved morphology. The present overall process is summarized in Scheme 4 below:

Scheme 4

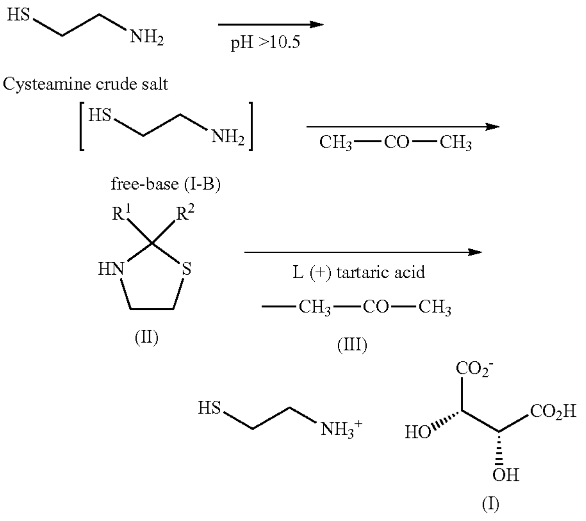

First, the Applicant has identified particularly favourable conditions for the preparation of the intermediate 2,2-disubstituted-thiazolidine (II), discovering that the conventional reaction of the Cysteamine salt with the required ketone, if carried out one—pot at a highly basic pH, provides for smooth ring closure to thiazolidine at mild temperatures and short times.

Under very basic environment, the ring closure is fast, without needing water removal to complete, the presence of by-products is minimized and the resulting thiazolidine is stable. Moreover, the high purity and stability of the 2,2-disubstituted-thiazolidine so prepared, allow a simple and fast isolation of the product by liquid/liquid separation instead of requiring longer purification procedures, often implying high thermal stress such as, for instance, high temperature distillation.

Advantageously, the raw thiazolidine (II) is obtained with high yields and purity and can be directly used in subsequent reactions.

Furthermore, the Applicant has found that the reaction of the intermediate crude thiazolidine (II), prepared according to the present process, with L(+)-tartaric acid to directly provide Cysteamine Bitartrate under the present process conditions, not only make the process straightforward, significantly reducing the number of steps, but also provides for a crude Cysteamine Bitartrate (I) of high purity and yield. The present overall process, as demonstrated in the following experimental section, is thus advantageous in general over prior art processes and in particular over the closest known route of synthesis shown in the Technical Disclosure and Indian patent application IN202041000697A commented above.

Finally, the Applicant has developed a crystallization process of Cysteamine Bitartrate that provides for an advantageous crystalline anhydrous Cysteamine Bitartrate (polymorph L2) powder, characterized by particle size (granulometry) and particle shape (morphology). The present powder of Cysteamine Bitartrate of the invention shows superior purity and stability compared with crystalline Cysteamine Bitartrate batches available on the market, which are prepared according to different synthetic routes and crystallized from other solvents, as shown in the experimental part.

Additionally, this peculiar powder form obtained thanks to the present crystallization conditions—characterized by the addition of the aqueous Cysteamine Bitartrate solution to the anti-solvent 2-propanol (herein named "inverse addition")—provide for a Cysteamine Bitartrate powder with improved appearance, increased bulk density and finer particles if compared with the product obtained according to the prior art by "direct addition". These powder features are predictive of better rheological properties, in particular of a better flowability.

It is thus an object of the present invention a process for the manufacture of crude Cysteamine Bitartrate of formula (I)

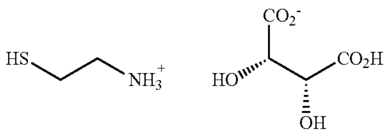

(I)

that comprises:

a) providing a thiazolidine of formula

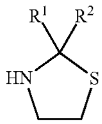

(II)

in which R1 and R2 are independently selected from H, linear or branched $C_1$-$C_{20}$ alkyls, optionally substituted $C_6$-$C_{20}$ aryls and optionally substituted heteroaryls, b) reacting the thiazolidine (II) with L(+)-tartaric acid in an aqueous medium, thus providing crude Cysteamine Bitartrate (I) in the aqueous medium, and c) isolating crude Cysteamine Bitartrate (I) from the aqueous medium, wherein the thiazolidine of formula (II) is prepared according to a one-pot process that comprises:

d) providing a Cysteamine salt, e) contacting the Cysteamine salt with a base in an aqueous medium at a pH of not less than 10.5, thus providing Cysteamine free base of formula (I-B)

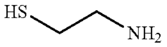

(I-B)

f) reacting the Cysteamine free base (I-B) in the same aqueous medium, with a compound of formula (III)

R1-CO—R2 (III)

in which R1 and R2 have the meanings reported above, thus providing the crude thiazolidine (II) and, optionally, g) purifying the thiazolidine of formula (II).

Preferably, the present process for the manufacture of crude Cysteamine Bitartrate of formula (I) further comprises after step b) the step h) of precipitating crude Cysteamine Bitartrate (I) by pouring the aqueous medium from step b) into 2-propanol (inverse addition) and then c) isolating the precipitated crude wet Cysteamine Bitartrate (I) from the aqueous medium.

The above process can further comprise after step c) the step of i) drying the precipitated crude wet Cysteamine Bitartrate (I), thus providing crude Cysteamine Bitartrate (I).

A further object of the present invention is a one-pot process for manufacturing the thiazolidine of formula (II) of the above process

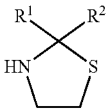

(II)

in which R1 and R2 are independently selected from H, linear or branched $C_1$-$C_{20}$ alkyls, optionally substituted $C_6$-$C_{20}$ aryls and optionally substituted heteroaryls that comprises:

d) providing a Cysteamine salt e) contacting the Cysteamine salt with a base in an aqueous medium at a pH of not less than 10.5, thus providing Cysteamine free base of formula (I-B)

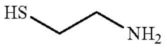

(I-B)

f) reacting one-pot the Cysteamine free base (I-B), in the same aqueous medium, with a compound of formula (III)

R1-CO—R2 (III)

in which R1 and R2 have the meanings reported above, thus providing the crude thiazolidine (II) and, optionally, g) purifying the thiazolidine of formula (II).

A further object of the present invention is a process for purifying crude Cysteamine Bitartrate, preferably obtained according to the invention, comprising the steps of:

h1) providing a solution of crude Cysteamine Bitartrate (I) in water h2) pouring said water solution of crude Cysteamine Bitartrate (I) into 2-propanol (inverse addition) thus precipitating crystalline Cysteamine Bitartrate (I) from the admixture, h3) isolating crystalline Cysteamine Bitartrate (I) from the crystallization medium and, preferably, i) drying the isolated crystalline Cysteamine Bitartrate (I), thus providing pure Cysteamine Bitartrate (I).

A further object of the present invention is a process for the preparation of crystalline anhydrous Cysteamine Bitartrate (I) (polymorph L2) that comprises the steps of:

d) providing a Cysteamine salt e) contacting the Cysteamine salt with a base in an aqueous medium at a pH of not less than 10.5, thus providing Cysteamine free base of formula (I-B)

(I-B)

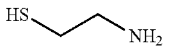

f) reacting one-pot the Cysteamine free base (I-B), in the same aqueous medium, with a compound of formula (III)

R1-CO—R2 (III)

in which R1 and R2 are independently selected from H, linear or branched $C_1$-$C_{20}$alkyls, optionally substituted $C_6$-$C_{20}$ aryls and optionally substituted heteroaryls, thus a) providing a crude thiazolidine of formula (II)

(II)

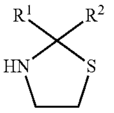

in which R1 and R2 have the meanings reported above, b) reacting the crude thiazolidine (II) with L(+)-tartaric acid in an aqueous medium, thus providing crude Cysteamine Bitartrate of formula (I (I)

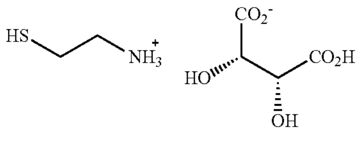

h) precipitating the crude Cysteamine Bitartrate (I) from the aqueous medium from step b) by pouring it into 2-propanol (inverse addition) and then c) isolating the precipitated crude wet Cysteamine Bitartrate (I) from the aqueous medium, h1) providing a solution of said crude wet Cysteamine Bitartrate (I) in water, h2) pouring said water solution of crude Cysteamine Bitartrate (I) into 2-propanol (inverse addition) thus precipitating crystalline Cysteamine Bitartrate (I), h3) isolating said crystalline Cysteamine Bitartrate (I) from the crystallization medium and i) drying the isolated crystalline Cysteamine Bitartrate (I) up to a water content lower than 1.0% ww, measured by Karl-Fischer method, thus providing crystalline anhydrous Cysteamine Bitartrate (I) (polymorph L2).

A further object of the present invention is a process for the preparation of crystalline monohydrate Cysteamine Bitartrate (I) (polymorph L1) that comprises the steps of:

d) providing a Cysteamine salt e) contacting the Cysteamine salt with a base in an aqueous medium at a pH of not less than 10.5, thus providing Cysteamine free base of formula (I-B)

(I-B)

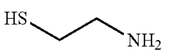

f) reacting one-pot the Cysteamine free base (I-B), in the same aqueous medium, with a compound of formula (III)

R1-CO—R2 (III)

in which R1 and R2 are independently selected from H, linear or branched $C_1$-$C_{20}$alkyls, optionally substituted $C_6$-$C_{20}$ aryls and optionally substituted heteroaryls, thus a) providing a crude thiazolidine of formula (II)

(II)

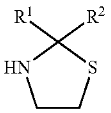

in which R1 and R2 have the meanings reported above, b) reacting the crude thiazolidine (II) with L(+)-tartaric acid in an aqueous medium, thus providing crude Cysteamine Bitartrate of formula (I)

(I)

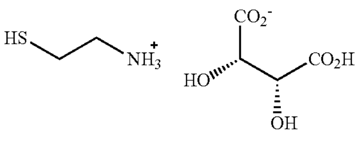

h) precipitating the crude Cysteamine Bitartrate (I) from the aqueous medium from step b) by pouring it into 2-propanol (inverse addition) and then c) isolating the precipitated crude wet Cysteamine Bitartrate (I) from the aqueous medium, h1) providing a solution of said crude wet Cysteamine Bitartrate (I) in water, h2) pouring said solution of crude Cysteamine Bitartrate (I) in water into 2-propanol (inverse addition) thus precipitating crystalline Cysteamine Bitartrate (I), h3) isolating said crystalline Cysteamine Bitartrate (I) from the crystallization medium and i) drying the isolated crystalline Cysteamine Bitartrate (I) up to a water content from 7.0% to 8.0% ww, measured by Karl-Fischer method, thus providing crystalline monohydrate Cysteamine Bitartrate (I) (polymorph L1).

A further object of the present invention is a process for the preparation of crystalline anhydrous Cysteamine Bitartrate (I) (polymorph L2) that comprises the steps of h1) providing a solution of Cysteamine Bitartrate (I) in water, h2) pouring said water solution of Cysteamine Bitartrate (I) into 2-propanol thus precipitating crystalline Cysteamine Bitartrate (I) from the admixture, preferably by cooling, h3) isolating crystalline Cysteamine Bitartrate (I) from the crystallization medium, and, i) drying the isolated crystalline Cysteamine Bitartrate (I), up to a water content lower than 1.0% ww, measured by Karl-Fischer method, thus providing crystalline anhydrous Cysteamine Bitartrate (I) (polymorph L2).

A further object of the present invention is a process for the preparation of crystalline monohydrate Cysteamine Bitartrate (I) (polymorph L1) that comprises the steps of h1) providing a solution of Cysteamine Bitartrate (I) in water, h2) pouring said water solution of Cysteamine Bitartrate (I) into 2-propanol thus precipitating crystalline Cysteamine Bitartrate (I) from the admixture, preferably by cooling, h3) isolating crystalline Cysteamine Bitartrate (I) from the crystallization medium, and, i) drying the isolated crystalline Cysteamine Bitartrate (I), up to a water content form 7.0% to 8.0% ww, measured by Karl-Fischer method, thus providing crystalline monohydrate Cysteamine Bitartrate (I) (polymorph L1).

A further object of the present invention is a process for converting crystalline monohydrate Cysteamine Bitartrate (I) (polymorph L1) into crystalline anhydrous Cysteamine Bitartrate (I) (polymorph L2) that comprises heating crystalline monohydrate Cysteamine Bitartrate (I) (polymorph L1) at a temperature of at least 45° C. and, preferably, at a pressure lower than 200 mbar up to a water content lower than 1.0% ww, preferably lower than 0.5% ww, measured by Karl-Fischer method. A further object of the present invention is Cysteamine Bitartrate obtainable according to any one of the processes of the present invention.

A further object of the present invention is a crystalline anhydrous Cysteamine Bitartrate (I) (polymorph L2) powder, preferably obtained according to the processes of the invention, said powder being characterized by a water content lower than 1.0%, measured by Karl-Fischer method, a volumetric particle size distribution (PSD), without micronization and after a pre-sieving with a sieve with openings of 600 microns, characterized by D50 not greater than 150 microns and D90 not greater than 250 microns, measured according to the method reported in the description, a bulk density from 0.28 g/ml to 0.35 g/ml, preferably around 0.30 g/ml measured according to Ph. Eur. 2.9.34, a tapped density from 0.40 g/ml to 0.43 g/ml, preferably around 0.42 g/ml measured according to Ph. Eur. 2.9.34 and/or a Hausner ratio from 1.30 to 1.55, preferably around 1.40.

DETAILED DESCRIPTION OF THE INVENTION

Figure 1:
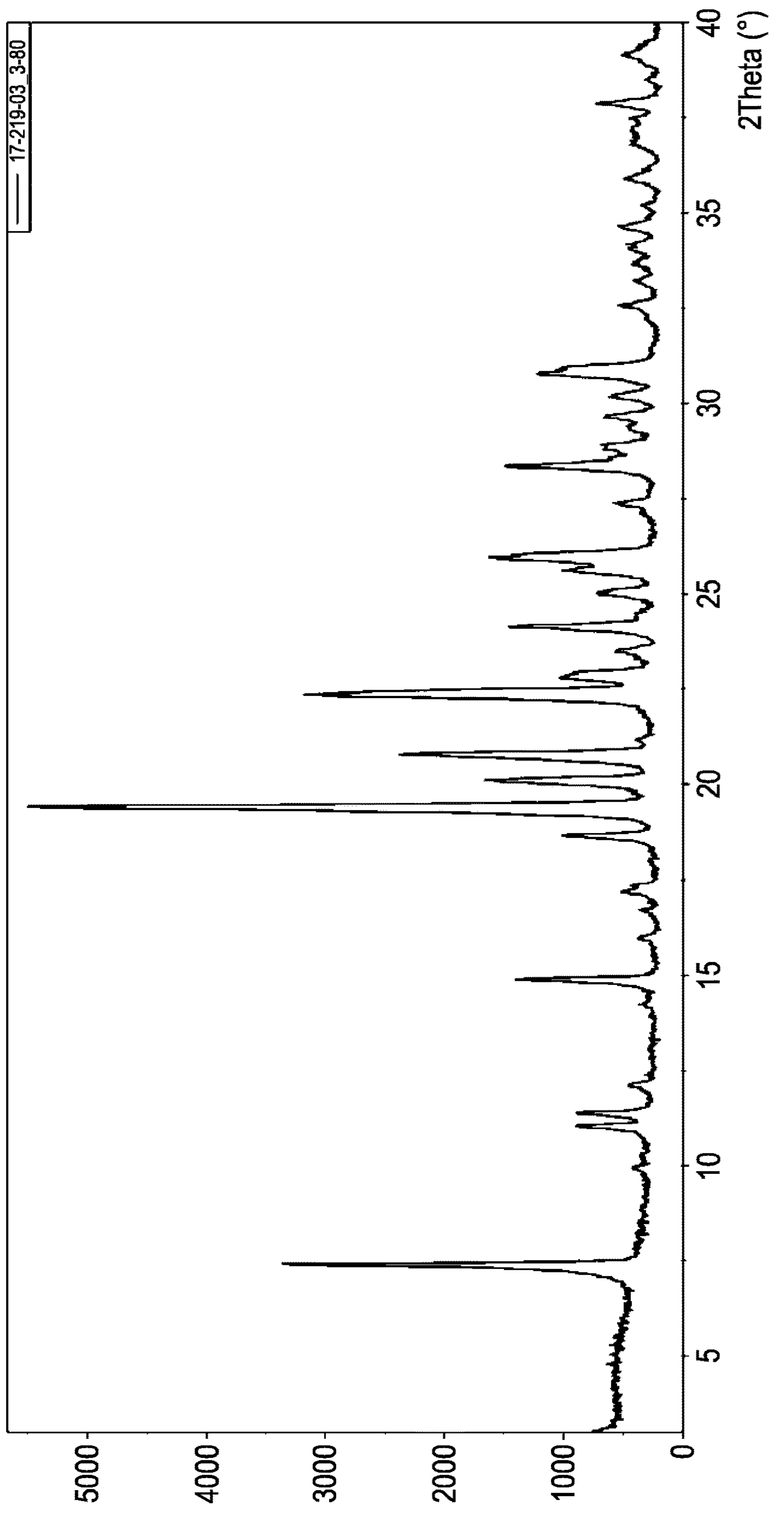
FIG. 1 shows the diffractogram of crystalline anhydrous Cysteamine Bitartrate (I) (polymorph L2) of Example 4. The analysis was carried out immediately after vial opening at room conditions (T=22.2° C., RH=28.5%).

The objects of the invention are characterized by the following features, taken alone or in combination. The preferences expressed in the following description for the intermediates, the conditions of process steps and the products, can apply, mutatis mutandis, to the intermediates, the conditions and the products of any embodiment of the invention.

An object of the present invention is a process for the manufacture of crude Cysteamine Bitartrate of formula (I)

(I)

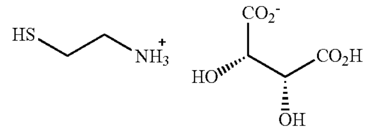

that comprises:

a) providing a thiazolidine of formula (II)

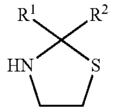

in which R1 and R2 are independently selected from H, linear or branched C1-C20 alkyls, optionally substituted C6-C20 aryls and optionally substituted heteroaryls, b) reacting the thiazolidine (II) with L(+)-tartaric acid in an aqueous medium, thus providing crude Cysteamine Bitartrate (I) in the aqueous medium, and c) isolating crude Cysteamine Bitartrate (I) from the aqueous medium, preferably by pouring said aqueous medium into 2-propanol (inverse addition) and then separating the precipitated crude Cysteamine Bitartrate (I), wherein the thiazolidine of formula (II) is prepared according to a one-pot process that comprises:

d) providing a Cysteamine salt, e) contacting the Cysteamine salt with a base in an aqueous medium at a pH of not less than 10.5, thus providing Cysteamine free base of formula (I-B)

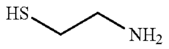

(I-B)

f) reacting the Cysteamine free base (I-B) in the same aqueous medium, with a compound of formula (III)

R1-CO—R2 (III)

in which R1 and R2 have the meanings reported above, thus providing the crude thiazolidine (II) and, optionally, g) purifying the thiazolidine of formula (II).

In the present process, the thiazolidine of formula (II) preferably has R1 and R2, the same or different, selected from H, alkyl $C_1$-$C_3$, such as methyl, ethyl, propyl or isopropyl, $C_6$-$C_{10}$ aryls such as phenyl or benzyl. Preferably at least one of R1 and R2 is different from H, more preferably both R1 and R2 are different from H, still more preferably R1 and R2 are selected from alkyl $C_1$-$C_3$, most preferably R1 and R2 are both methyl.

The thiazolidine of formula (II) of step a) is prepared according to the process of the present invention comprising steps d) to f) and, optionally, g) as described later on. Preferably, the thiazolidine (II) of step a) has a purity higher than 70%, more preferably higher than 80%, even more preferably higher than 90% measured by GC according to the method described in the present experimental section.

The thiazolidine of formula (II) and the L(+) tartaric acid are reacted in step b) in a molar ratio preferably from 1:1 to 1:2, more preferably from 1:1 to 1:1.5, even more preferably from 1:1 to 1:1.1 or most preferably in a stoichiometric ratio of about 1:1. As the person skilled in the art knows, the same reaction can be carried out with D(−) tartaric acid or with (t) tartaric acid, however it is preferably carried out with L(+) tartaric acid as this optical isomer is the natural product, easily available and cheap. The reaction of the thiazolidine (II) with the L (+)-tartaric acid can be carried out in suspension or, preferably in solution.

Step b) of the process for preparation of Cysteamine Bitartrate (I) from the thiazolidine (II) is carried out in an aqueous medium. The aqueous medium can comprise an admixture of water and at least a solvent.

The amount of water in the reaction medium is at least the stoichiometric amount requested for the hydrolytic opening of the thiazolidine ring, but preferably water is used in excess, more preferably the aqueous medium consists of water.

The optional solvent can be preferably selected from organic polar solvents such as alcohols like methanol, ethanol, butanol, propanol; nitriles like acetonitrile, propionitrile, butyronitrile; ethers like tetrahydrofuran, dioxane, dimethoxyethane; esters like ethyl acetate, ethyl acetoacetate, butyl acetate, propyl acetate; ketones like acetone, methyl ethyl ketone, methyl isobutyl ketone; other polar solvents like dimethylformamide, dimethyl sulfoxide and mixtures thereof.

Preferably, the concentration of the thiazolidine (II) in the reaction medium of step b) is from 15 to 30% by weight, more preferably from 20 to 25% by weight vs the reaction medium weight.

Preferably, as Cysteamine is easily oxidized to Cystamine (disulphide by-product 2,2'-dithio-bis-ethanamine), the present processes are carried out under inert atmosphere, such as for instance under nitrogen or argon and/or in the presence of an antioxidant agent, such as for instance butylated hydroxy anisole, butylated hydroxy toluene, thiosulfate salts, and the like.

The Applicant found that the reaction of step b) carried out under acidic conditions, preferably at a pH from 2.0 to 5.0, more preferably at a pH from 3.5 to 4.0, and inert atmosphere minimizes Cystamine formation. Accordingly, the content of Cystamine in the crude Cysteamine Bitartrate prepared according to the present process is preferably lower than 1.0%, more preferably lower than 0.5% or 0.3%, measured by HPLC according to the method of the present experimental section.

In the present process, the thiazolidine (II) can be used as free-base or as a salt. In case of a salt, the thiazolidine free base can be released—previously or in situ—by addition of a suitable base, before the addition of the L (+)-tartaric acid.

Preferably, the thiazolidine of formula (II) and the L(+) tartaric acid are reacted in step b) at a temperature from 40° C. to 55° C., more preferably from 48° C. to 52° C., preferably for a time of at least 3 hours, more preferably from about 3 hours to 5 hours.

Preferably, the reaction of step b) is brought to completeness by removing the compound of formula (III) R1-CO—R2 that is formed in the hydrolysis, preferably, for low-boiling compounds, by distillation.

When R1-CO—R2 is acetone (R1=R2=$CH_3$) preferably the distillation is carried out at temperature not higher than 50° C., to prevent distillation of the starting thiazolidine (II).

Preferably, the removal of the ketone (III) by distillation is repeated more than once and each time the volume removed is replaced with an equivalent volume of the medium, preferably of water.

Finally, according to step c), the crude Cysteamine Bitartrate can be isolated from the reaction residue through conventional work up methods such as for instance, removal of the aqueous solvent by evaporation, preferably forming an azeotropic admixture with suitable solvents to facilitate the evaporation, as known in the art, or more preferably by extraction in an organic phase, followed by anhydrification and concentration by distillation of the solvent.

In one embodiment, the crude Cysteamine Bitartrate is isolated from the aqueous reaction medium by direct precipitation according to step h), preferably followed by one or more crystallizations, preferably according to the purifying process object of the present invention comprising steps h1-h3) and then preferably dried as per step i), to provide first a crude Cysteamine Bitartrate and then a purer crystalline Cysteamine Bitartrate.

In a preferred embodiment of step c), the aqueous reaction medium from step b), after complete removal of the compound of formula (III) by distillation, is poured into 2-propanol (inverse addition) and crude Cysteamine Bitartrate is directly precipitated from this admixture (step h).

Preferably, the volume ratio between 2-propanol and water at the end of the inverse addition of step h) described above is from 10:1 to 2.5:1, more preferably from 5:1 to 2.8:1, even more preferably is around 3:1.

Preferably, in step h) the concentration of the crude Cysteamine Bitartrate in the water solution is from 520 to 330 g/Kg, more preferably from 500 to 440 g/Kg.

In the present inverse addition of step h), 2-propanol can comprise minor amounts of other solvents in admixture such as for instance less than 50%, 40%, 30%, 20%, 10% or 5% of polar solvents such as water, nitriles or other short chain alcohols such as ethanol, methanol and the like.

In one embodiment of step h) 2-propanol is not used in admixture with any other solvent.

The precipitated crude Cysteamine Bitartrate can be separated from the medium by conventional techniques such as for instance by filtration or centrifugation.

The crude wet cake of Cysteamine Bitartrate (I) can be dried thus providing crude Cysteamine Bitartrate (I) or can be subjected to further purification by crystallization. In a preferred embodiment, the present process, from the thiazolidine (II) to the crude Cysteamine Bitartrate (I) obtained by direct precipitation from the reaction medium after distillation of the ketone described above (steps a) to i), typically provides for a yield of at least 72% mol, preferably of at least 77% mol.

The crude Cysteamine Bitartrate directly precipitated from the admixture of water and 2-propanol typically has a purity of at least 97%, preferably of at least 98%, more preferably of at least 99% measured by HPLC according to the method described in the present experimental section.

A preferred process for the manufacture of crude Cysteamine Bitartrate of formula (I) according to the invention is characterized in that

- the thiazolidine of formula (II) has R1=R2=methyl,
- the thiazolidine of formula (II) and the L(+) tartaric acid are reacted in step b) in a molar ratio from 1:1 to 1:1.5, preferably from 1:1 to 1:1.1,
- the thiazolidine of formula (II) and the L(+) tartaric acid are reacted in step b) at a temperature from 45° C. to 55° C., and
- the crude Cysteamine Bitartrate is isolated from the aqueous reaction medium from step b) by pouring said aqueous reaction medium, after complete removal of the compound of formula (III) by distillation, in 2-propanol thus directly precipitating crude Cysteamine Bitartrate.

A further object of the present invention is a process for manufacturing the thiazolidine of formula (II)

(II)

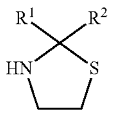

a useful intermediate for the manufacture of Cysteamine Bitartrate according to the present invention.

In the thiazolidine of formula (II), R1 and R2 are preferably independently selected from H, alkyl $C_1$-$C_3$, such as methyl, ethyl, propyl or isopropyl, $C_8$-$C_{10}$ aryls such as phenyl or benzyl. Preferably at least one of R1 and R2 is different from H, more preferably both R1 and R2 are different from H, still more preferably R1 and R2 are selected from alkyl $C_1$-$C_3$, most preferably R1 and R2 are both methyl.

The present process for the manufacture of thiazolidine (II) comprises:

d) providing a Cysteamine salt, e) contacting the Cysteamine salt with a base in an aqueous medium at a pH of not less than 10.5, thus providing Cysteamine free base of formula I-B (I-B)

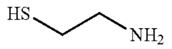

f) reacting one-pot the Cysteamine free base (I-B) in the same aqueous medium, with a compound of formula (III)

R1-CO—R2 (III)

in which R1 and R2 preferably have the meanings reported above, thus providing the crude thiazolidine (II) and, optionally, g) purifying the thiazolidine of formula (II).

The starting Cysteamine salt of step d) can be selected from inorganic or organic salt. Inorganic salt can be selected for instance from hydrochloride, hydrobromide, hydroiodide salt and the like. Organic salt can be selected for instance from formate, acetate, fumarate, propionate, butyrate, valerate, oxalate, maleate, citrate, glutarate, succinate, salicylate and the like.

Preferably, Cysteamine salt is selected from hydrochloride, hydrobromide, hydroiodide, more preferably is Cysteamine Hydrochloride.

Preferably, the Cysteamine salt is suspended or, preferably, dissolved in an aqueous solvent preferably selected from water, methanol, ethanol, 2-propanol and their admixtures, more preferably in water.

Preferably, the Cysteamine salt is present in the reaction medium in a concentration by weight from 10 to 50%, preferably from 15 to 30%.

Differently from the previous processes, in the present process the pH of the reaction medium of step e) is not less than 10.5, preferably not less than 11, more preferably not less than 12, even more preferably not less than 12.5.

Preferably, the pH of the reaction medium is between 12 and 14, more preferably between 12.5 and 13.5. Advantageously, a pH not less than 10.5 provides for an easy and quick ring closure to the desired thiazolidine (II). The applicant observed that a lower pH causes incomplete release of Cysteamine free-base, which, in addition to causing a loss in yield, can lead to a lower purity of the desired thiazolidine due to side reactions. In fact, because of the incomplete Cysteamine release, the resulting acetone in excess can self-condense or provide other impurities such as thiazepine.

At the pH of the process of the invention, the SH function of Cysteamine free base is also partly deprotonated. Furthermore, at the pH values of the process of the invention, the thiazolidine is present as free-base that can be easily purified by simple direct extraction from the aqueous to the organic phase during work up. Preferably, the base used to bring the pH of the reaction medium of step e) at a value of not less than 10.5 is selected from organic bases such as NaOMe, NaOEt, NaOi-Pr, $Et_3N$, (i-Pr)2NEt (DIPEA) or inorganic bases such as NaOH, $Na_2CO_3$, $NaHCO_3$, more preferably the base is selected from NaOEt, $Na_2CO_3$ and NaOH, even more preferably is NaOH.

In the present process, in respect of the Cysteamine salt, the base is used in a molar ratio at least sufficient to completely release Cysteamine free base (I-B) from the salt. Preferably, the base is used in excess, more preferably in 10% mol excess, providing a pH of the medium not less than 10.5, preferably not less than 11, more preferably not less than 12, even more preferably not less than 12.5.

In the present process, the Cysteamine free base (I-B) is not isolated but is reacted in situ in step f), in the same aqueous medium, with the desired compound of formula (III) R1-CO—R2 (one pot reaction).

Suitable aldehydes and ketones of formula R1-CO—R2 (III) are for instance formaldehyde, acetaldehyde, acetone, methyl ethyl ketone, benzaldehyde, vanillin, preferably acetone.

Preferably, the molar ratio between R1-CO—R2 (III) and Cysteamine is from 2:1 to 1:1, more preferably from 1.2:1 to 1:1, even more preferably from 1.1:1 to 1:1.

Preferably, the present reaction is carried out at a temperature not higher than 25° C., more preferably not higher than 18° C., most preferably between 10 and 15° C. The Applicant noted that at temperatures higher than 25° C. there is an increase formation of by-products.

Preferably, the present reaction is carried out under inert atmosphere, such as for instance under nitrogen, and/or in the presence of an antioxidant agent, such as for instance sodium thiosulfate and the like.

The final thiazolidine can be isolated from the reaction medium and possibly purified by conventional methods (step g).

Preferably, the aqueous reaction medium is extracted with an organic solvent immiscible with water, such as for instance dichloromethane or cyclohexane, preferably with cyclohexane, which is more selective than other solvents in extracting the desired product.

Preferably, before extraction, the aqueous phase is salted by addition of conventional salts, such as NaCl, in order to facilitate the salting-out and the extraction of the thiazolidine into the organic phase.

Preferably, before removing the organic solvent by distillation, the organic phases are anhydrified by conventional techniques such as for instance by addition of sodium sulphate and the like. The Applicant observed that the removal of water before starting concentration and distillation operations is advisable to minimize the degradation of the final product.

The organic phases, after removal of the solvent by distillation, provide the crude thiazolidine (II) that can be advantageously used as such in the preparation of Cysteamine Bitartrate according to the steps a)-c) of the present process without further purification.

Preferably, in order to minimize the loss of the thiazolidine thus obtaining high yields and to recycle the organic solvent, the distillation is carried out in more than one step, collecting the organic solvent separately from the azeotropic admixture of the solvent with the ketone (III), under temperature and pressure conditions that, as the skilled person knows, depend on the solvent and the ketone used in the specific reaction. Preferably, in case of 2,2-dimethylthiazolidine, the distillation is carried out at a temperature not higher than 40° C. and at a pressure not lower 80 mbar.

Advantageously, the present process, carried out at a pH of not less than 10.5, preferably not less than 11, more preferably not less than 12, even more preferably not less than 12.5, provides for crude thiazolidine with an unexpected purity, with a thiazolidine content of at least 98%, preferably at least 99% measured by GC as described in the present experimental section.

Preferably, the present process provides for the thiazolidine with a yield higher than 70%, more preferably higher than 72%. The advantages of the present process of manufacture of thiazolidine (II) and of the thiazolidine (II) so obtained are apparent from the present experimental part that describes a prior art preparation of a thiazolidine (II) and its conversion into crude Cysteamine Bitartrate (see Example 7A and 7C).

Preferred process conditions for the manufacture and use of the thiazolidine (II) in the preparation of crude Cysteamine Bitartrate of formula (I) according to the invention are

- the Cysteamine salt of step d) is Cysteamine Hydrochloride,
- the pH of the aqueous medium of step e) is between 12.5 and 13.5,
- the compound of formula R1-CO—R2 (III) in step f) is acetone,
- the reaction of step f) is carried out at a temperature not higher than 25° C., and
- the crude thiazolidine (II) obtained from steps d) to f) is used as such in the preparation of crude Cysteamine Bitartrate according to the steps a) to c).

In a particularly preferred embodiment, the present process for the manufacture of thiazolidine (II) is carried out at the following conditions: pH around 13, temperature form 10 to 15° C. and molar ratio Cysteamine Hydrochloride to acetone of about 1:1.

A preferred overall process for the manufacture of crude Cysteamine Bitartrate of formula (I) from step a) to step i) according to the invention is characterized in that:

- the Cysteamine salt of step d) is Cysteamine Hydrochloride,
- the pH of the aqueous medium of step e) is between 12.5 and 13.5,
- the compound of formula R1-CO—R2 (III) in step f) is acetone,
- the reaction of step f) is carried out at a temperature not higher than 25° C.,
- the crude thiazolidine (II) obtained from steps d) to f) is used as such in the preparation of crude Cysteamine Bitartrate according to the steps a) to c),
- the thiazolidine of formula (II) has R1=R2=methyl,
- the thiazolidine of formula (II) and the L(+) tartaric acid are reacted in step b) in a molar ratio from 1:1 to 1:1.5, preferably from 1:1 to 1:1.1,
- the thiazolidine of formula (II) and the L(+) tartaric acid are reacted in step b) at a temperature from 45° C. to 55° C., and
- the crude Cysteamine Bitartrate is isolated from the aqueous reaction medium from step b) by directly pouring said aqueous reaction medium, after complete removal of the compound of formula (III) by distillation, in 2-propanol thus directly precipitating crude Cysteamine Bitartrate.

The crude Cysteamine Bitartrate prepared according to the present process can be further purified, preferably by crystallization, to provide the desired purer crystalline Cysteamine Bitartrate. Preferably the purification is carried out according to the present invention, by dissolving crude Cysteamine Bitartrate in water and then by pouring this aqueous solution of Cysteamine Bitartrate into 2-propanol (inverse addition, steps h1 and h2), followed by isolation of the product (step h3) and, preferably, drying (step i).

It is thus a further object of the present invention a process for purifying crude Cysteamine Bitartrate, preferably obtained according to the invention, comprising the steps of:

h1) providing a solution of crude Cysteamine Bitartrate (I) in water, h2) pouring said water solution of crude Cysteamine Bitartrate (I) into 2-propanol (inverse addition) thus precipitating crystalline Cysteamine Bitartrate (I) from the admixture, h3) isolating crystalline Cysteamine Bitartrate (I) from the crystallization medium and, preferably, i) drying the isolated crystalline Cysteamine Bitartrate (I), thus providing pure Cysteamine Bitartrate (I).

In the present purification process, the solution of crude Cysteamine Bitartrate (I) in water of step h1) can be directly the aqueous reaction medium of step b) above, an aqueous solution prepared by dissolution in water of the isolated precipitated crude Cysteamine Bitartrate from step h) above or any suitable water solution of any crude Cysteamine Bitartrate.

Preferably the crude Cysteamine Bitartrate (I) has an HPLC purity of at least 90%, preferably of at least 95%, more preferably of at least 97%. Preferably, the volume ratio between 2-propanol and water, at the end of the inverse addition of step h2) described above, is from 10:1 to 2.5:1, more preferably from 5:1 to 2.8:1, even more preferably around 3:1.

Preferably, the concentration of the crude Cysteamine Bitartrate in the water solution of step h1) and h2) is from 1100 to 500 g/A, more preferably from 1000 to 800 g/l or from 520 to 330 g/Kg, more preferably from 500 to 440 g/Kg.

In the present inverse addition of step h2), 2-propanol can comprise minor amounts of other solvents in admixture such as for instance less than 50%, 40%, 30%, 20%, 10% or 5% of polar solvents such as water, nitriles or other short chain alcohols such as ethanol, methanol and the like.

Depending on the conditions of step i) the wet cake of crystalline Cysteamine Bitartrate can be dried to provide crystalline monohydrate Cysteamine Bitartrate (polymorph L1) or crystalline anhydrous Cysteamine Bitartrate (polymorph L2).

Preferably, crystalline monohydrate Cysteamine Bitartrate (L1) is formed by heating the wet cake from step h3) at a temperature lower than 40° C., preferably lower than 35° C. and preferably higher than 25° C., at a pressure lower than 200 mbar, preferably lower than 100 mbar, more preferably lower than 50 mbar and preferably for a time from 2 to 24 hours.

Preferably, crystalline monohydrate Cysteamine Bitartrate (L1) is prepared by drying the wet cake up to a water content from 7.0% to 7.5% ww, more preferably of about 7.3% ww, measured by Kari-Fischer method.

A water content even higher than 8% is of course possible for crystalline monohydrate Cysteamine Bitartrate (L1) not completely dried.

Preferably, crystalline anhydrous Cysteamine Bitartrate (L2) is prepared by heating the wet cake from step h3) or the cake partially dried of crystalline monohydrate Cysteamine Bitartrate (L1) at temperature of at least 40° C., preferably of at least 45° C., more preferably at least 50° C. and not higher than 70° C., preferably not higher than 60° C., at a pressure lower than 200 mbar, preferably lower than 100 mbar, more preferably lower than 50 mbar and for a time preferably from 2 to 24 hours (step i). Preferably, crystalline anhydrous Cysteamine Bitartrate (L2) is prepared by drying the wet cake up to water content lower than 1.0% ww, more preferably lower than 0.9% or 0.5% ww, measured by Karl-Fischer method.

Advantageously, the above process can be used to purify the crude Cysteamine Bitartrate, obtained according to the process of the invention or to any other process. The crystallized anhydrous Cysteamine Bitartrate (I) has a HPLC purity greater than 98.0%, preferably greater than 99.0%, more preferably greater than 99.7%.

In the present description with the term "pure Cysteamine Bitartrate" a Cysteamine Bitartrate with a HPLC purity, measured according to the method reported in the present experimental section, generally higher than 98.0%, preferably higher than 99.0%, more preferably greater than 99.7% is meant.

A further object of the present invention is a process for the preparation of crystalline anhydrous Cysteamine Bitartrate (I) (polymorph L2) that comprises the steps of:

d) providing a Cysteamine salt e) contacting the Cysteamine salt with a base in an aqueous medium at a pH of not less than 10.5, thus providing Cysteamine free base of formula (I-B)

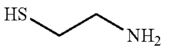

(I-B)

f) reacting one-pot the Cysteamine free base (I-B), in the same aqueous medium, with a compound of formula (III)

R1-CO—R2 (III)

in which R1 and R2 are independently selected from H, linear or branched $C_1$-$C_{20}$ alkyls, optionally substituted $C_6$-$C_2$ aryls and optionally substituted heteroaryls, thus a) providing a crude thiazolidine of formula (II)

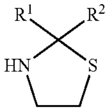

(II)

in which R1 and R2 have the meanings reported above, b) reacting the crude thiazolidine (II) with L(+)-tartaic acid in an aqueous medium, thus providing crude Cysteamine Bitartrate of formula (I)

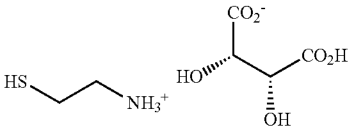

(I)

h) precipitating the crude Cysteamine Bitartrate (I) from the aqueous medium from step b) by pouring it into 2-propanol (inverse addition) and then c) isolating the precipitated crude wet Cysteamine Bitartrate (I) from the aqueous medium, h1) providing a solution of said crude wet Cysteamine Bitartrate (I) in water, h2) pouring said solution of crude Cysteamine Bitartrate (I) in water into 2-propanol (inverse addition) thus precipitating crystalline Cysteamine Bitartrate (I), h3) isolating said crystalline Cysteamine Bitartrate (I) from the crystallization medium and i) drying the isolated crystalline Cysteamine Bitartrate (I) up to a water content lower than 1.0% ww, measured by Karl-Fischer method, thus providing crystalline anhydrous Cysteamine Bitartrate (I) (polymorph L2).

Preferably, in step i) the isolated crystalline Cysteamine Bitartrate (I) is dried up to a water content lower than 0.9%, or lower than 0.5% ww, measured by Karl-Fisher method.

Preferably in the drying step i) the isolated crystalline Cysteamine Bitartrate (I) is dried by heating at a temperature of at least 40° C., preferably at least 45° C., more preferably at least 50° C. and not higher than 70° C., preferably not higher than 60° C. Preferably, in the drying step i) the isolated crystalline Cysteamine Bitartrate (I) is dried by heating at a pressure lower than 200 mbar, preferably lower than 100 mbar, more preferably lower than 50 mbar, even more preferably lower than 10 mbar. Preferably, in the drying step i) the isolated crystalline Cysteamine Bitartrate (I) is dried by heating for a time from 2 to 24 hours.

The preferences and conditions, previously reported for the partial processes above, apply alone or in combination to the present overall process as well.

The final crystalline anhydrous Cysteamine Bitartrate (I) (polymorph L2) prepared according to the present process typically has a HPLC purity greater than 98%, preferably greater than 99%.

The purity of the final Cysteamine Bitartrate can be further increased by repeating the present crystallization process several times.

The present whole process for the manufacture of Cysteamine Bitartrate according to the present invention, due to the straightforward reaction of L (+)-tartaric acid with the intermediate thiazolidine (II) and to the minimization of intermediate work up and purification steps provides for high yields.

The overall yield of the present process from the Cysteamine salt to the crystallized anhydrous Cysteamine Bitartrate (I) (polymorph L2) is typically of at least 35% mol % ww, preferably of at least 45% mol, even more preferably of at least 55% mol.

Advantageously, inert gas can be applied through the whole synthesis process and even to packaging operations, to preserve intermediate and final products from undesired oxidative side reactions.

A further object of the present invention is a process for the preparation of crystalline monohydrate Cysteamine Bitartrate (I) (polymorph L1) that comprises the steps of:

d) providing a Cysteamine salt e) contacting the Cysteamine salt with a base in an aqueous medium at a pH of not less than 10.5, thus providing Cysteamine free base of formula (I-B)

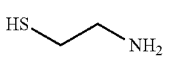

(I-B)

f) reacting one-pot the Cysteamine free base (I-B), in the same aqueous medium, with a compound of formula (III)

R1-CO—R2 (III)

in which R1 and R2 are independently selected from H, linear or branched $C_1$-$C_2$ alkyls, optionally substituted $C_6$-$C_{20}$ aryls and optionally substituted heteroaryls, thus a) providing a crude thiazolidine of formula (II)

(II)

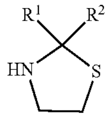

in which R1 and R2 have the meanings reported above, b) reacting the crude thiazolidine (II) with L(+)-tartaric acid in an aqueous medium, thus providing crude Cysteamine Bitartrate of formula (I)

(I)

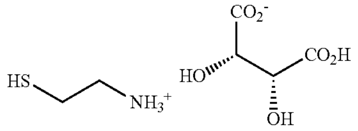

h) precipitating the crude Cysteamine Bitartrate (I) from the aqueous medium from step b) by pouring it into 2-propanol (inverse addition) and then c) isolating the precipitated crude wet Cysteamine Bitartrate (I) from the aqueous medium, h1) providing a solution of said crude wet Cysteamine Bitartrate (I) in water, h2) pouring said solution of crude Cysteamine Bitartrate (I) in water into 2-propanol (inverse addition) thus precipitating crystalline Cysteamine Bitartrate (I), h3) isolating said crystalline Cysteamine Bitartrate (I) from the crystallization medium and i) drying the isolated crystalline Cysteamine Bitartrate (I) it up to a water content from 7.0% to 8.0% ww, measured by Karl-Fischer method, thus providing crystalline monohydrate Cysteamine Bitartrate (I) (polymorph L1).

Preferably, in the drying step i) the isolated crystalline Cysteamine Bitartrate (I) is dried by heating up to a water content from 7.0% to 7.5% ww, more preferably of about 7.3% ww.

Preferably, in the drying step i) the isolated crystalline Cysteamine Bitartrate (I) is dried by heating at a temperature lower than 40° C., more preferably lower than 35° C. and preferably higher than 25° C.

Preferably, in the drying step i) the isolated crystalline Cysteamine Bitartrate (I) is dried by heating at a pressure lower than 200 mbar, preferably lower than 100 mbar, more preferably lower than 50 mbar.

Preferably, in the drying step i) the isolated crystalline Cysteamine Bitartrate (I) is dried by heating for a time from 2 to 24 hours.

The same preferences in the conditions of steps h1) to i) recited above or below apply herein as well.

A further object of the present invention is a process for the preparation of crystalline monohydrate Cysteamine Bitartrate (I) (polymorph L1) that comprises the steps of h1) providing a solution of Cysteamine Bitartrate (I) in water, h2) pouring said water solution of Cysteamine Bitartrate (I) into 2-propanol thus precipitating crystalline Cysteamine Bitartrate (I) from the admixture, preferably by cooling, h3) isolating crystalline Cysteamine Bitartrate (I) from the crystallization medium, and, i) drying the isolated crystalline Cysteamine Bitartrate (I), up to a water content form 7.0% to 8.0% ww, measured by Karl-Fischer method, thus providing crystalline monohydrate Cysteamine Bitartrate (I) (polymorph L1).

A further object of the present invention is a process for the preparation of crystalline anhydrous Cysteamine Bitartrate (I) (polymorph L2) that comprises the steps of h1) providing a solution of Cysteamine Bitartrate (I) in water, h2) pouring said water solution of Cysteamine Bitartrate (I) into 2-propanol thus precipitating crystalline Cysteamine Bitartrate (I) from the admixture, preferably by cooling, h3) isolating crystalline Cysteamine Bitartrate (I) from the crystallization medium, and, i) drying the isolated crystalline Cysteamine Bitartrate (I), up to a water content lower than 1.0% ww, measured by Karl-Fischer method, thus providing crystalline anhydrous Cysteamine Bitartrate (I) (polymorph 12).

The same preferences in the conditions of steps h1) to i) recited above or below apply herein as well.

The crystallization processes of Cysteamine Bitartrate described in the prior art used methanol (U.S. Ser. No. 10/251,850), admixtures of methanol and 2-propanol (U.S. Ser. No. 10/221,132), ethanol (Acta Cryst. 2013, 658-664) or 2-propanol added as anti-solvent to aqueous admixture (direct addition, IN202041000697A) as crystallization solvents.

The commercial anhydrous Cysteamine Bitartrate mentioned in the present Example 5 was crystallized from ethanol while the product of the present Example 10B from 2-propanol/water (direct addition) (comparison products)

The Applicant, after undertaking experimental studies, has understood that Cysteamine Bitartrate form L1 described in U.S. Ser. No. 10/251,850 corresponds to the monohydrate Cysteamine Bitartrate form, which is also characterized in Acta Cryst. (2013), C69, 658-664 and IN202041000697A as Form M, while Cysteamine Bitartrate form L2 described in U.S. Ser. No. 10/251,850 is the anhydrous form.

Advantageously, the present crystallization process results in a crystalline Cysteamine Bitartrate of superior purity, stability and improved powder appearance. In particular, the present crystallization process by inverse addition of Cysteamine Bitartrate water solution to 2-propanol very effectively removes impurities and provides for a powder with better properties if compared with previous powders, in particular with the powder obtained according to direct addition of 2 propanol mentioned above.

In the present description, the terms “crystalline polymorph” and “crystalline polymorph powder” both refer to the crystalline polymorph solid form.

According to the present crystallization process, in step h1) said solution of Cysteamine Bitartrate (I) in water can be either the same aqueous reaction medium comprising crude Cysteamine Bitartrate (I) obtained after step b) of the present process or any other aqueous solution of Cysteamine Bitartrate prepared ex novo from isolated crude or partially purified Cysteamine Bitartrate.

In one embodiment, said aqueous solution is prepared by isolation of crude Cysteamine Bitartrate (I) from said aqueous reaction medium after steps b) and c) followed by dissolution of the isolated crude Cysteamine Bitartrate (I) in water.

In step h1) of the present crystallization process the concentration of Cysteamine Bitartrate (I) in the water solution, before contacting with 2-propanol, is preferably from 1100 to 500 g/l, more preferably from 1000 to 800 g/A (g of product per litre of solvent) or from 520 to 330 g/Kg, more preferably from 500 to 440 g/Kg (g of product per Kg of admixture).

In one embodiment, in step h1) of the present process, Cysteamine Bitartrate (I) is dissolved in water preferably by heating, preferably at a temperature not higher than 60° C., more preferably at a temperature between 45 and 55° C.

According to the present process, the solution of Cysteamine Bitartrate in water of step h1) can be prepared by dissolving any form of Cysteamine Bitartrate or by forming Cysteamine Bitartrate in situ for instance from Cysteamine and L(+) tartaric acid, preferably in a molar ratio from 1:2 to 1:1, more preferably in equimolar amount.

Preferably, the solution of Cysteamine Bitartrate in water of step h1) can be prepared starting from the isolated Cysteamine Bitartrate of step h3) or, more preferably, by directly using the reaction aqueous medium containing the crude Cysteamine Bitartrate obtained from step b).

According to the present crystallization process, in step h2) the solution of Cysteamine Bitartrate in water is contacted by inverse addition with 2-propanol, optionally in admixture with water, thus precipitating, preferably by cooling, the crystalline Cysteamine Bitartrate (I).

Preferably, at the end of the inverse addition of step h2), the volume ratio of 2-propanol and water in the crystallization admixture of step h2) is from 10:1 to 2.5:1, more preferably from 5:1 to 2.8:1, even more preferably around 3:1.

The crystallization admixture can comprise other solvents in minor amount; however, the solvent admixture preferably consists of 2-propanol and water, preferably in the ratios specified above.

In step h2), the solution of Cysteamine Bitartrate in water is poured into 2-propanol, optionally in admixture with water or minor amounts of other solvents as previously mentioned (inverse addition), thus providing after isolation and drying up to a water content lower than 1% by weight, a powder of crystalline anhydrous Cysteamine Bitartrate (I) (polymorph L2) particularly fine, non-sticky and with improved appearance.

Preferably, the inverse addition of the water solution into 2-propanol is made slowly, in a time which depends on the scale of the reaction but indicatively may range from 30 minutes to 2 hours or more. Preferably, during the addition, the admixture is kept under vigorous stirring. The Applicant noted that a slow addition together with a vigorous stirring advantageously provides for a non-sticky powder with low particle size dimensions.

In one embodiment, in particular in case of recrystallization of crystalline quite pure Cysteamine Bitartrate to further increase purity, the inverse addition of the water solution is made to an admixture of 2-propanol and water.

Preferably, the precipitation of the desired crystalline form is facilitated by seeding with pure crystals of that form, such as crystals of the crystalline anhydrous Cysteamine Bitartrate (I) (polymorph L2).

The crystalline Cysteamine Bitartrate can be precipitated from the mixture of step h2) preferably by cooling to a temperature between 15 and 35° C., more preferably between 15 and 25° C., even more preferably between 18 and 22° C.

In step h3) of the present process, crystalline Cysteamine Bitartrate can be isolated from the crystallization mixture by applying one or more conventional techniques known in the art such as filtration, concentration, removal of solvent by evaporation, distillation, centrifugation, decantation, cooling, flash evaporation, drying on rotavapor and the like.

Preferably, the isolated crystallized Cysteamine Bitartrate is dried in step i) by conventional techniques such as, for instance, in oven under vacuum, with a residual pressure lower than 200 mbar, preferably lower than 100 mbar, more preferably lower than 50 mbar, at 25-60° C. for a period of 2-24 hours.

Depending on the drying conditions, it is possible to obtain monohydrate or anhydrous Cysteamine Bitartrate, respectively having a water content from 7.0% to 8.0% ww or lower than 1.0% ww, measured by Karl-Fischer method.

According to the invention, one or more steps from h1), h2), h3) and i) can be advantageously carried out under inert atmosphere such as under nitrogen.

The dried anhydrous crystalline Cysteamine Bitartrate can be preferably sieved, in order to remove coarse particles (e.g. particles having at least one dimension equal to or higher than 600 microns), if present, and/or be micronized according to conventional techniques to provide even finer particles of dimensions more suitable for a particular final use.

A particularly preferred process for the preparation of crystalline anhydrous Cysteamine Bitartrate (I) (polymorph L2) according to the invention comprises the steps of:

h1) providing a solution of Cysteamine Bitartrate (I) in water, in which the concentration of Cysteamine Bitartrate (I) is from 1100 to 800 g/l or from 500 to 440 g/Kg;

h2) contacting said solution of Cysteamine Bitartrate (I) in water with 2-propanol, in which the volume ratio of 2-propanol and water is from 11:1 to 3:1, wherein said contacting comprises:

slowly adding in a time preferably of at least 1 hour said water solution of Cysteamine Bitartrate (I) to 2-propanol (inverse addition), under stirring and at a temperature between 20 and 35° C., keeping the mass under stirring for at least 30 minutes at a temperature preferably from 30 to 35° C. and then cooling preferably at 18-22° C. preferably in about 2 hours, keeping under stirring at 18-22° C. for preferably at least 16 hours, thus precipitating, crystalline Cysteamine Bitartrate (I);

h3) isolating crystalline Cysteamine Bitartrate from the crystallization medium, and i) drying the isolated crystalline Cysteamine Bitartrate (I), up to a water content lower than 1.0% ww, measured by Karl-Fischer method, thus providing crystalline anhydrous Cysteamine Bitartrate (I) (polymorph L2).

The duration of the addition of the aqueous solution, the temperatures and times of digestion and precipitation depicted above, provide for an improved crystalline powder form, with better filterability and flowability on visual inspection.

Advantageously, the crystalline anhydrous Cysteamine Bitartrate (I) (polymorph L2) if prepared according to the process of the present invention by pouring the aqueous solution of Cysteamine Bitartrate in 2-propanol (inverse addition), is in the form of a particularly fine powder, finer than the powders obtained from other prior solvent admixtures.

A further object of the present invention is a process for converting crystalline monohydrate Cysteamine Bitartrate (I) (polymorph L1) into crystalline anhydrous Cysteamine Bitartrate (I) (polymorph L2) that comprises heating crystalline monohydrate Cysteamine Bitartrate (I) (polymorph L1) at a temperature of at least 45° C. and, preferably, at a pressure lower than 200 mbar up to a water content lower than 1.0% ww, preferably lower than 0.5% ww, measured by Karl-Fischer method. Regarding the conversion process i) the temperature of heating the crystalline monohydrate Cysteamine Bitartrate (I) (polymorph L1) is preferably of at least 50° C. Preferably the temperature of heating is not higher than 70° C., more preferably not higher than 60° C.

The heating is carried out at a pressure preferably lower than 100 mbar, more preferably lower than 50 mbar, even more preferably lower than 10 mbar and for a time preferably from 2 to 24 hours.

The heating is carried out at up to water content preferably lower than 0.9% or 0.5% ww, measured by Karl-Fischer method.

A further object of the present invention is Cysteamine Bitartrate obtainable according to any one of the processes of the present invention.

In particular, a further object of the present invention is a crystalline anhydrous Cysteamine Bitartrate (I) (polymorph L2) powder, preferably obtained according to the processes of the invention, said powder being preferably characterized by a volumetric particle size distribution (PSD) after a pre-sieving with a sieve with openings of 600 microns, characterized by D50 not greater than 100 microns and D90 not greater than 150 microns, measured according to the method reported in the experimental part, a water content lower than 0.5%, measured by Karl-Fischer method, a bulk density from 0.29 g/ml to 0.32 g/ml, preferably around 0.30 g/ml measured according to Ph. Eur. 2.9.34, a tapped density from 0.41 g/ml to 0.43 g/ml, preferably around 0.42 g/ml measured according to Ph. Eur. 2.9.34, a Hausner ratio from 1.30 to 1.45, preferably around 1.40.

The present powder is made of particles characterized by small particle size (granulometry)—advantageously obtained without needing any micronization—with a uniform distribution and by particle shape (morphology) particularly suitable for pharmaceutical applications. As known in the art, technological properties of powders (bulk density, flowability, surface area, etc.) as well as the areas of their application strictly depend on particles characteristics.

In a preferred embodiment, the crystalline anhydrous Cysteamine Bitartrate (I) (polymorph L2), preferably prepared according to the inverse addition process of the present invention (steps h1-h3 and subsequent drying of step i), without needing any micronization and after a pre-sieving with a sieve having openings of 600 microns, has a volumetric particle size distribution (PSD) characterized by D50 not greater than 150 microns and D90 not greater than 250 microns, preferably D50 not greater than 100 microns and D90 not greater than 150 microns, measured according to the method reported in the experimental part.

Preferably, the sieving is carried out with a sieve having openings of 600 microns, to remove coarse particles.

The powder of crystalline anhydrous Cysteamine Bitartrate (I) (polymorph L2) obtained by the present inverse addition process is non-sticky and shows improved appearance. Furthermore, the powder properties e morphology are predictive of better filterability, stirrability, stability and flowability, which are of great value for drug development.

The bulk density of a powder is the ratio of the mass of an untapped powder sample to its volume. It depends on both the density of powder particles and the spatial arrangement of the particles in the powder bed. Preferably the present crystalline anhydrous Cysteamine Bitartrate (I) (polymorph L2) powder is characterized by a bulk density higher than 0.28 g/ml, more preferably higher than 0.29 g/ml, even more preferably higher than 0.30 g/ml, measured according to Ph. Eur. 2.9.34.

Preferably the present crystalline anhydrous Cysteamine Bitartrate (I) (polymorph L2) powder is characterized by a tapped density from 0.40 g/ml to 0.43 g/ml, preferably around 0.42 g/ml measured according to Ph. Eur. 2.9.34.

Preferably the present crystalline anhydrous Cysteamine Bitartrate (I) (polymorph L2) powder is characterized by a Hausner ratio from 1.30 to 1.55, preferably around 1.40.

Preferably, the crystalline anhydrous Cysteamine Bitartrate (I) (polymorph 12) powder of the invention is obtained according to the present manufacturing and crystallization process.

The present crystalline anhydrous Cysteamine Bitartrate (I) (polymorph L2) has been analysed by XRPD, DSC, DVS, IR, UV, $^{1}$H-NMR, $^{13}$C-NMR, mass spectra and HPLC.

The present crystalline anhydrous Cysteamine Bitartrate (I) (polymorph L2) is characterized by

Figure 2:
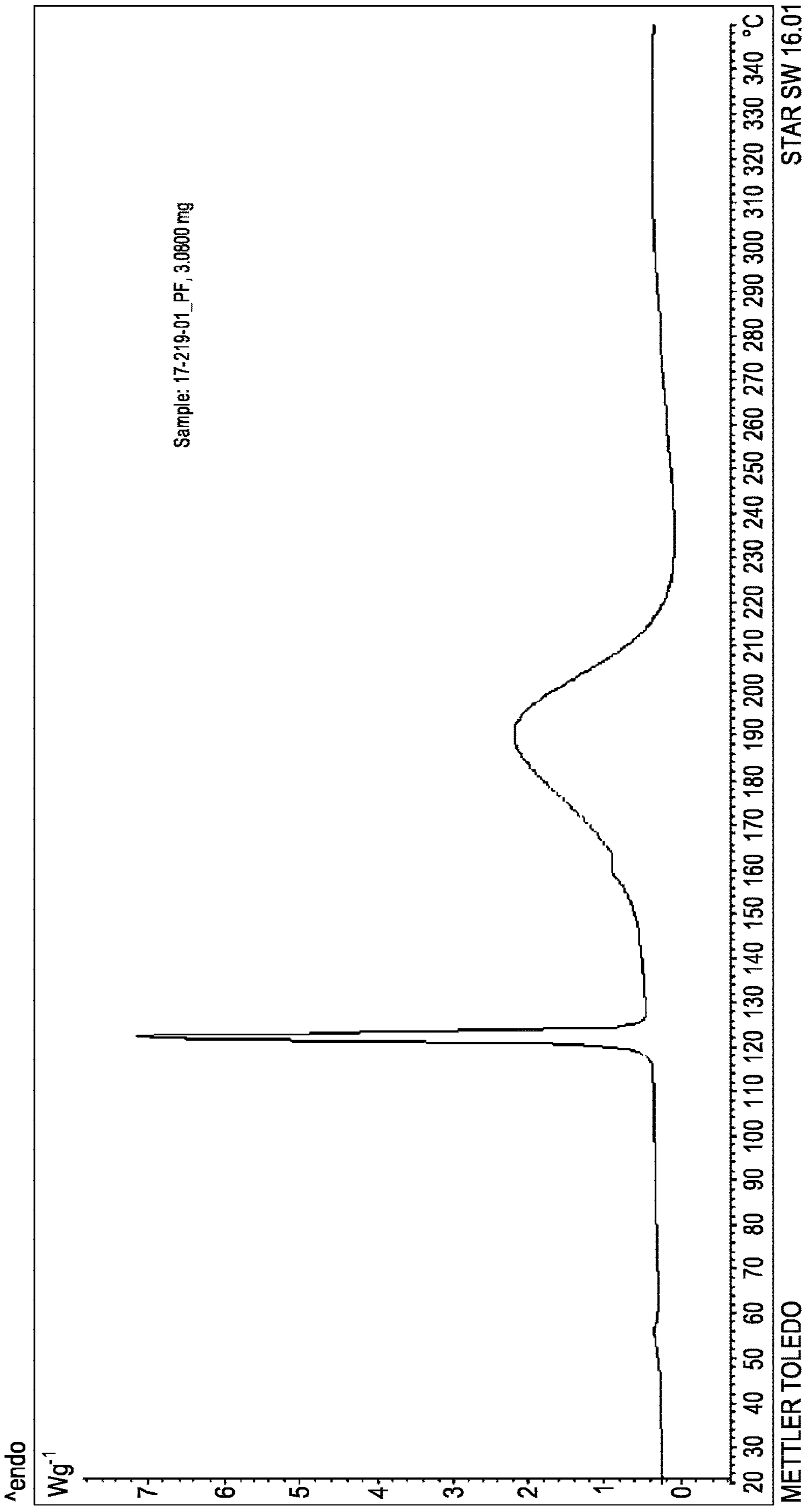
FIG. 2 is the DSC thermogram of crystalline anhydrous Cysteamine Bitartrate (I) (polymorph L2) of Example 4.
Figure 3:
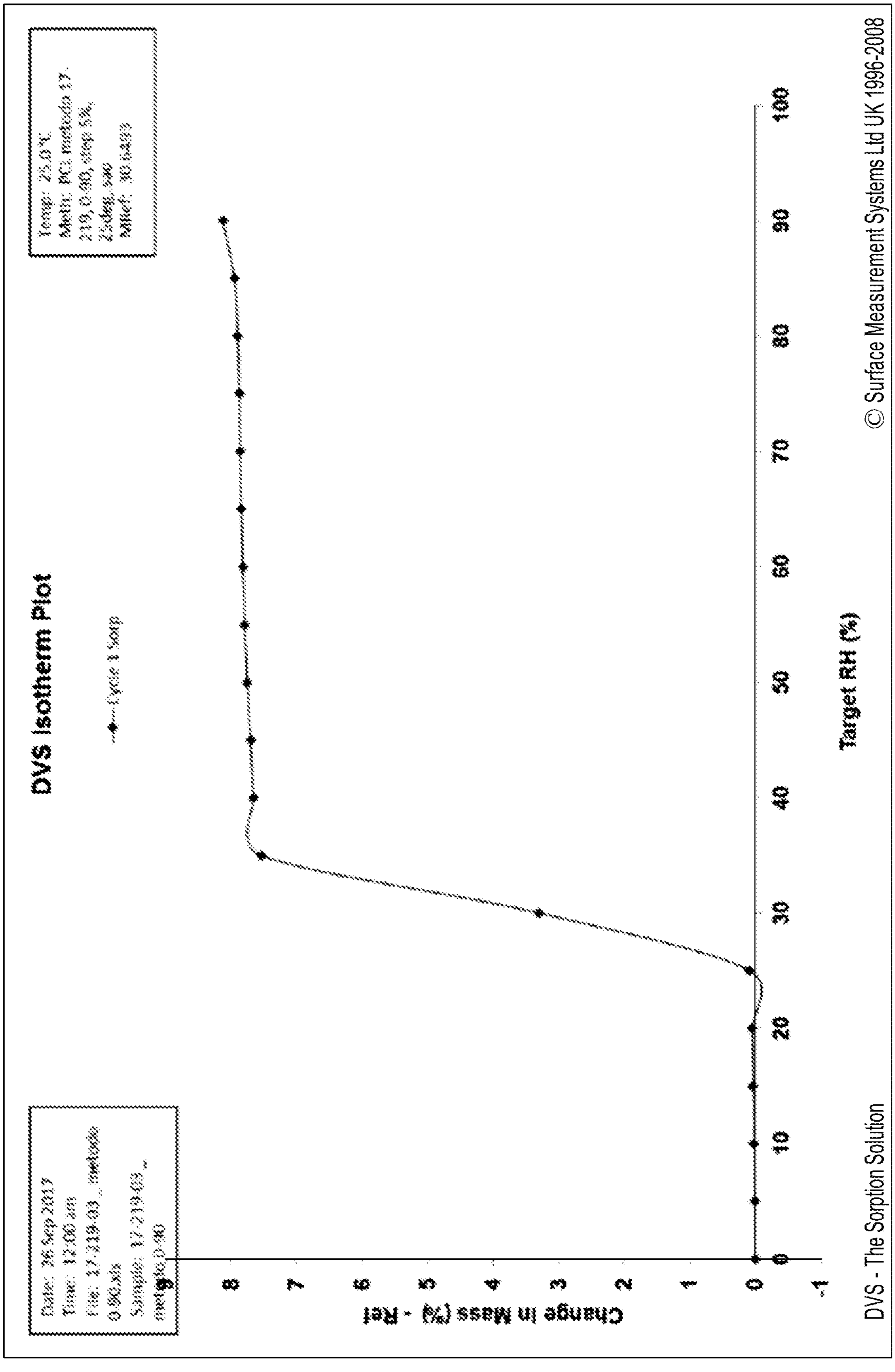
FIG. 3 shows the DVS graph of crystalline anhydrous Cysteamine Bitartrate (I) (polymorph L2) of Example 4.
Figure 4:
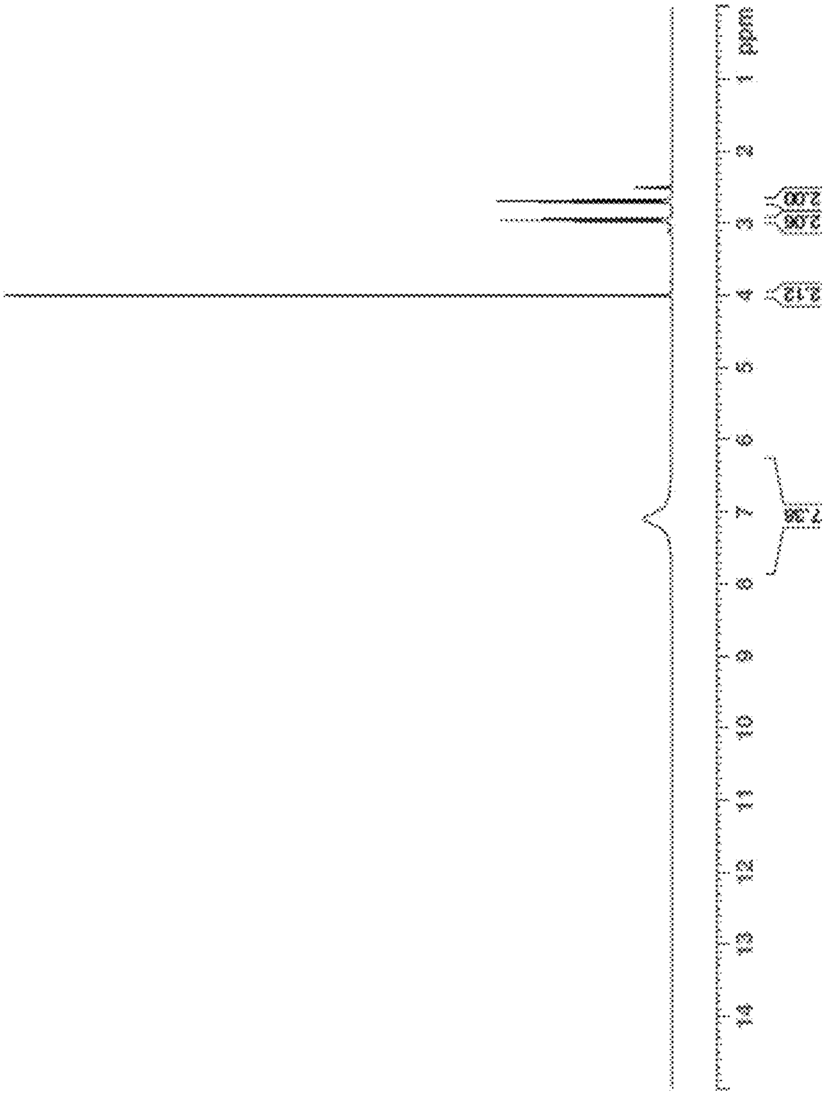
FIG. 4 shows the $^{1}$H-NMR spectrum of crystalline anhydrous Cysteamine Bitartrate (I) (polymorph L2) of Example 4.
Figure 5:
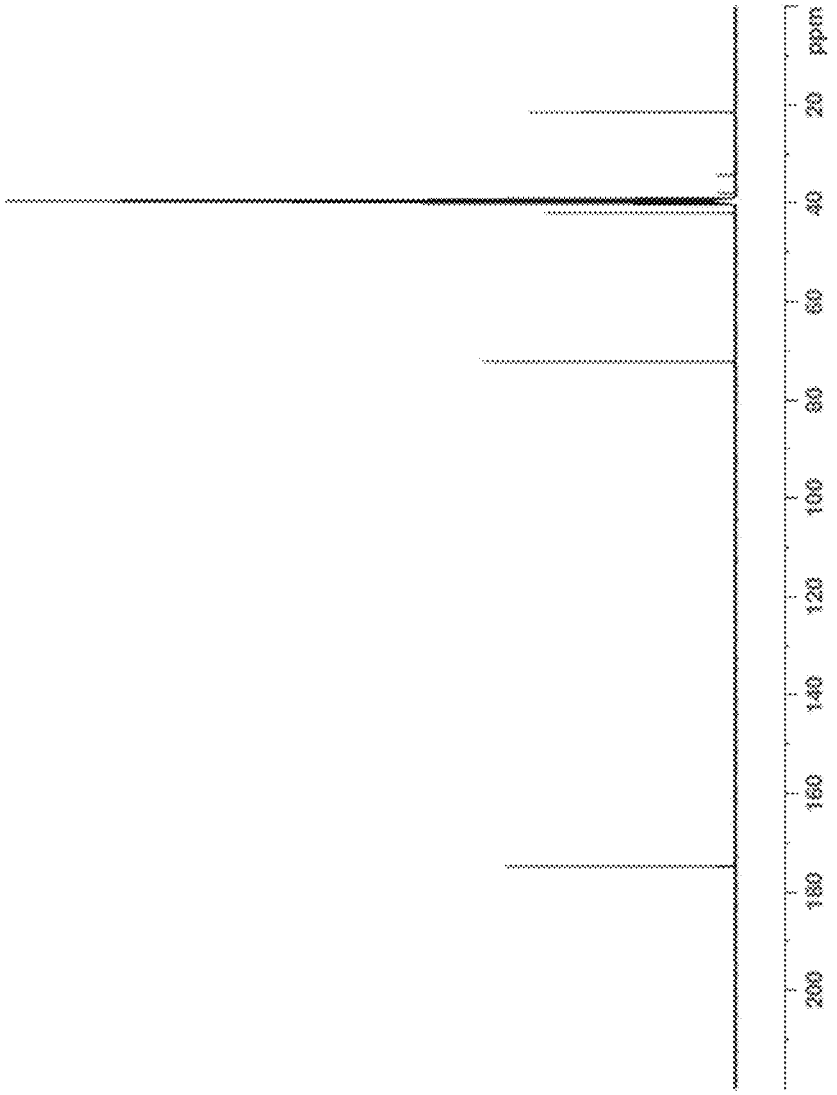
FIG. 5 shows the $^{13}$C-NMR spectrum of crystalline anhydrous Cysteamine Bitartrate (I) (polymorph L2) of Example 4.
Figure 6:
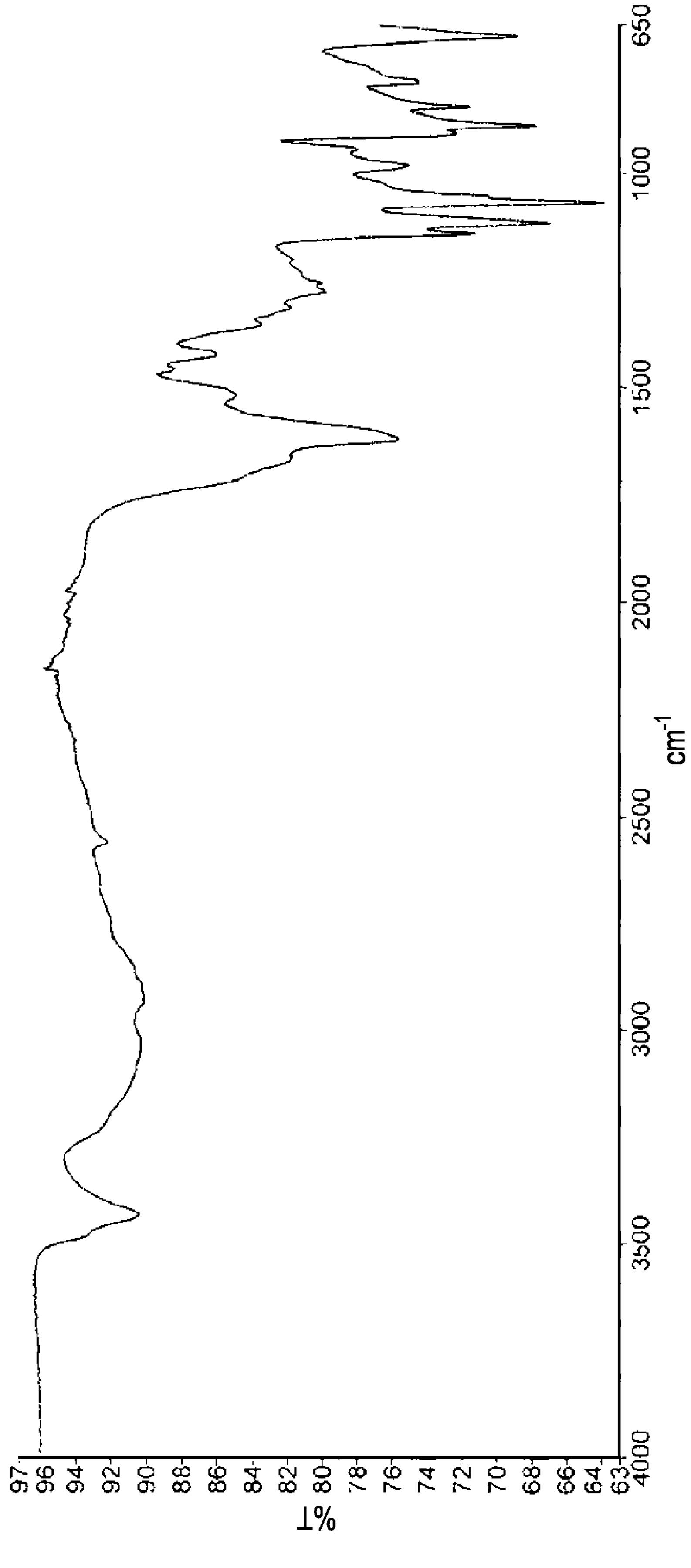
FIG. 6 shows the IR spectrum of crystalline anhydrous Cysteamine Bitartrate (I) (polymorph L2) of Example 4.
Figure 7:
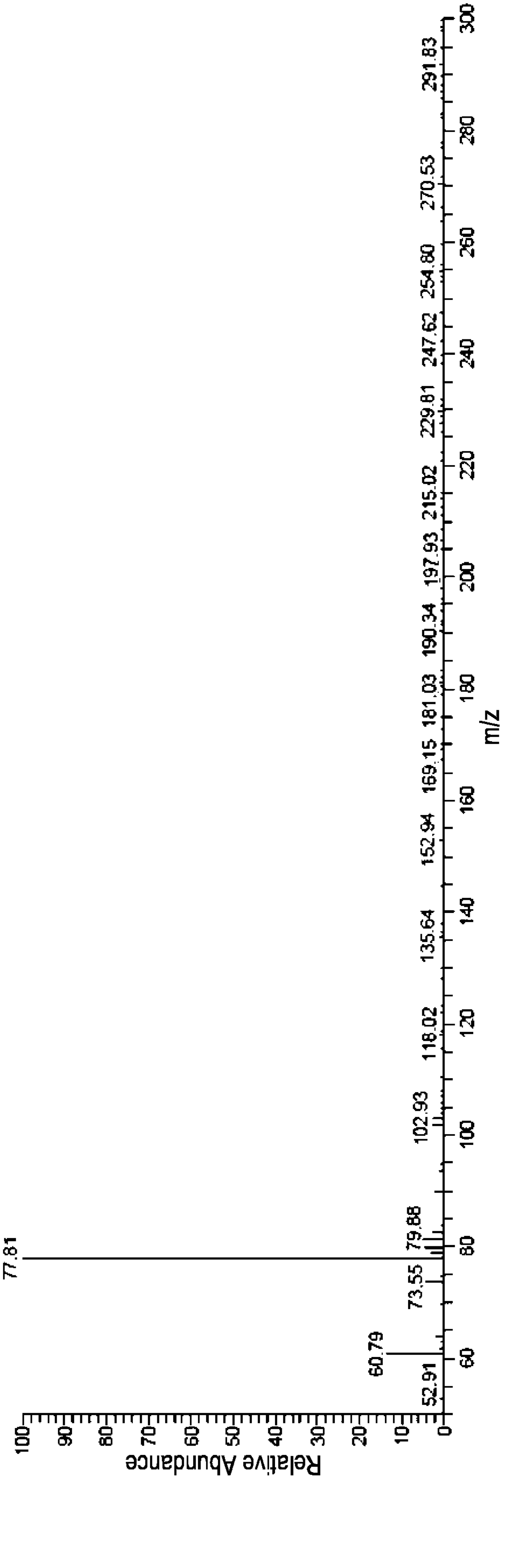
FIG. 7 shows the mass spectrum of crystalline anhydrous Cysteamine Bitartrate (I) (polymorph L2) of Example 4.
Figure 8:
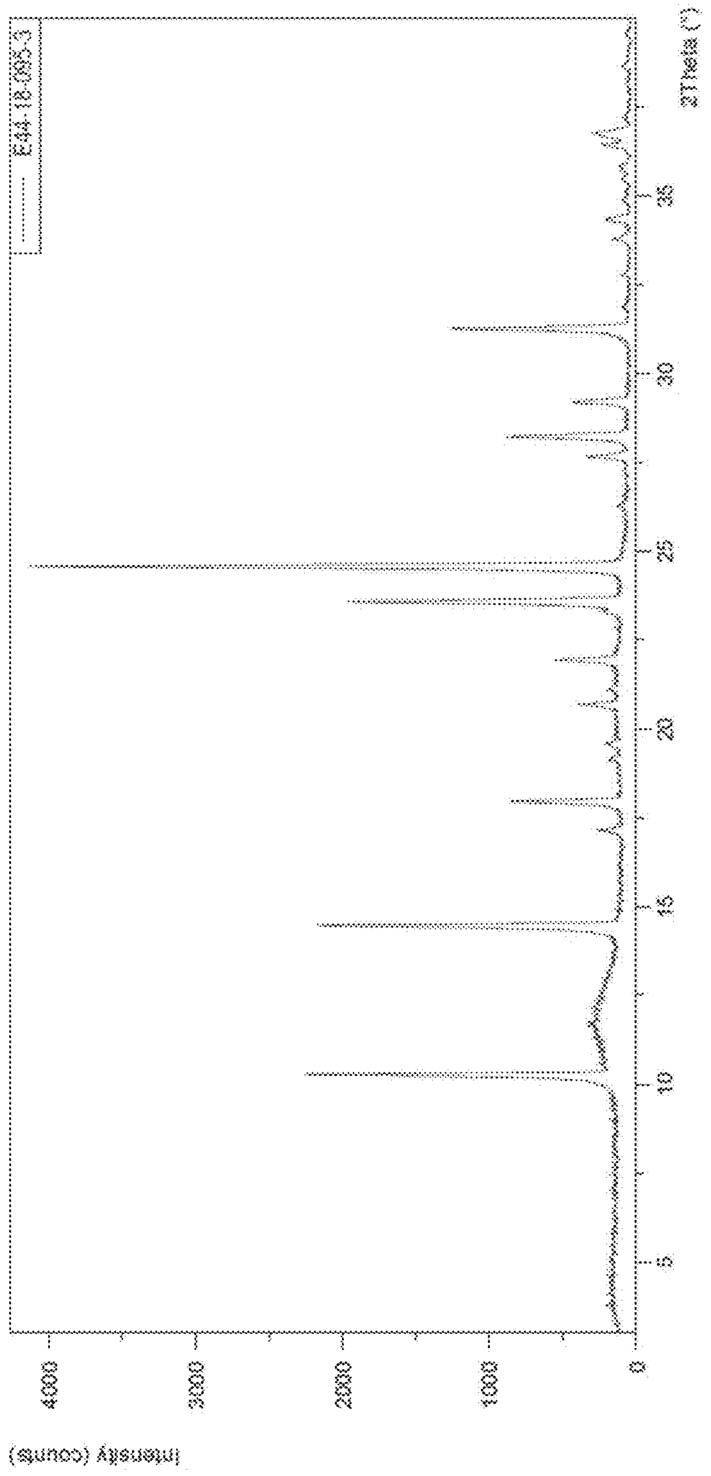
FIG. 8 shows the XRPD diffractogram of Cysteamine Bitartrate crystallized from water/2-propanol by direct addition according to Example 10 of IN202041000697A after drying at 30° C. under vacuum (present Example 10B, Form M, monohydrate).

- an X-ray powder diffraction pattern with characteristic diffraction peaks as disclosed in FIG. 1;
- a characteristic DSC peak at about 122° C., as shown in FIG. 2, measured according to the method and conditions reported in the present experimental part:
- a characteristic DVS graph as shown in FIG. 3;
- a characteristic $^{1}$H-NMR spectrum as shown in FIG. 4;
- a characteristic $^{13}$C-NMR spectrum as shown in FIG. 5;
- an IR spectrum compliant to the IR spectrum of the standard anhydrous crystalline Cysteamine Bitartrate as shown in FIG. 6; and
- a mass spectrum as shown in FIG. 7.

The crystalline anhydrous Cysteamine Bitartrate (I) (polymorph L2) obtained according to the present process is a white crystalline powder, preferably characterized by one or more of the following properties:

- a melting point in the range of 118-122° C., preferably of 120-122° C.
- a water content lower than 1.0%, preferably at most of 0.8%, measured by Karl-Fischer method
- an impurities total content, at release, of at most 1.5%, preferably at most 1.0%, more preferably at most 0.5% by HPLC;
- a volumetric particle size distribution (PSD), without micronization and after a pre-sieving with a sieve having openings of 600 microns for removing the coarse particles, characterized by D50 not greater than 150 microns and D90 not greater than 250 microns, preferably D50 not greater than 100 microns and D90 not greater than 150 microns, measured according to the method reported in the experimental part.

According to DVS analyses (see FIG. 3) the present crystalline anhydrous Cysteamine Bitartrate (I) (polymorph L2) started to convert into the hydrate form at 25% RH and 25° C., gaining 7.5% w/w of water (about 1 mol of $H_2O$).

It follows that the present crystalline anhydrous Cysteamine Bitartrate (I) (polymorph L2) is stable and does not rapidly convert into the hydrate form if stored at temperatures not higher than 25° C. and under an atmosphere having RH % not higher than 25% ww.

The present crystalline anhydrous Cysteamine Bitartrate (I) (polymorph L2) can be advantageously stored for long periods, according to the stability data reported under the present experimental section where the impurity content and profile remain consistent.

The present crystallization process provides Cysteamine Bitartrate (I) as anhydrous crystalline polymorph L2 with improvements in terms of purity, stability, bulk density and particle size distribution.

Without being bound to any particular theory, the Applicant believes that the high purity of the present crystallized Cysteamine Bitartrate and the crystallization conditions of the process of the invention probably influence the solid properties resulting in very fine particles and especially prevent the formation of particle aggregates, keeping the particle size distribution constant over time.

The Applicant realized that the present crystalline anhydrous Cysteamine Bitartrate (I) (polymorph L2) prepared according to the present process is characterized by a significant stability of the powder properties overtime.

The Applicant speculates that the advantageous particle size distribution stability of the present crystalline anhydrous Cysteamine Bitartrate (I) (polymorph L2) powder, in terms of absence of aggregates over other Cysteamine Bitartrate polymorph L2 powders, could derive, for instance, from the different morphology or from a different impurities profile of the present crystalline anhydrous Cysteamine Bitartrate (I) (polymorph L2) (e.g. different kind and/or amount of impurities as shown in the present experimental section, Example 5) which, at crystalline level, reduces the tendency of the particles to aggregate.

As the skilled person knows, these differences may be related to the presence or absence in the final product of certain by-products or solvents, which can mainly depend on the peculiar synthesis and/or crystallization process.

Furthermore, the smaller particle size of the present crystalline anhydrous Cysteamine Bitartrate (I) (polymorph L2) powder obtained thanks to the inverse addition process, could also be responsible for the minor propensity of the powder to aggregate and possibly be associated with a better dissolution profile in comparison with prior art powders.

The present invention is further illustrated by the following representative examples that are provided for illustrative purposes only.

Experimental Part

Analytical Methods

Cysteamine Bitartrate assay was carried out by titration with potassium iodate according to the method of European Pharmacopeia 2.2.20, using the following conditions: potassium iodate 0.1N solution, containing 3.567 g potassium iodate previously dried at 110° C. to constant weigh and 1000 ml of water, was prepared. 500.0 mg of the sample were weighted in a 250 ml flask. 100 ml of water, 10 ml of sulphuric acid 3.6 N, 1.0 g of KI and 2.0 ml of starch solution were added into the flask. The solution was titrated with potassium iodate solution to the end point (light blue persistent colour for more than 30 seconds). In parallel, a blank titration was performed.

1.0 ml of 0.1N potassium iodate solution was equivalent to 22.72 mg of Cysteamine Bitartrate.

$$\text{Assay }\%=\{[(Vc-Vb)\times 22.72\times N]/[mg\text{ sample}\times 0.1]\}\times 100$$

where:

Vc=Volume Potassium Iodate solution used to titrate the sample

Vb=Volume Potassium Iodate solution used to titrate the blank

N=Normality of Potassium Iodate solution

Free tartaric acid (TA assay) was assessed by titration with NaOH and Potassium Iodide. Free tartaric acid was calculated by the difference between the volumetric title with KIO3 t.q. and the title with NaOH 0.1 N according to the formula:

$$\text{Free Tartaric Acid}=(\text{Assay NaOH }\%-\text{Assay }KIO3)/2$$

If Assay with $KIO_3$ was higher than Assay with NaOH there was free Cysteamine.

Cysteamine, Cystamine and Impurities Content by HPLC

Cysteamine and impurities content were evaluated by HPLC according to method of European Pharmacopeia. 2.2.29, using the following conditions:

Chromatographic System

Column: Alltima C18 LL, I=250 mm, Ø=4.6 mm, 5 μm or equivalent

Column temperature: 25° C.,

Mobile phase A: 380 ml Water, 300 ml Acetonitrile, 320 ml Methanol and 1.4 ml $H_3PO_4$ 85%; stirred up to obtain a clear solution and then added with 11.52 g of Sodium Dodecylsulphate;

Mobile phase B: Acetonitrile

Flow rate: 1.4 ml/min; Detector: UV at 210 nm; Run time: 35 min; Injected volume: 20 μl.

Gradient as reported in Table 1 below:

TABLE 1

| Time (min) | Mobile phase A (% V/V) | Mobile phase B (% V/V) |
|---|---|---|
| 0 | 100 | 0 |
| 7 | 100 | 0 |
| 27 | 60 | 40 |
| 32 | 60 | 40 |
| 35 | 100 | 0 |
| 45 | 100 | 0 |

and elution times as per Table 2:

TABLE 2

| Compound | RT | RRT |
|---|---|---|
| Cysteamine Bitartrate | 4.6 | 1.0 |
| 2,2-dimethylthiazolidine | 5.4 | 1.2 |
| Cystamine | 15.3 | 3.3 |
| Di-Cysteamine acetonide | 18.1 | 3.9 |

Solutions a. Test solution: was prepared by dissolving about 100.0 mg of sample in 5.0 ml of water.

b. Cystamine 2HCl Reference solution (0.1%) was prepared by dissolving about 150.0 mg of Cystamine 2HCl in 200.0 ml of water (Cystamine 2HCl Std. mother solution). 2.0 ml of this solution is then diluted to 50.0 ml with water.

c. Cystamine 2HCl Reference solution (0.5%) was prepared by diluting 2.0 ml of Cystamine 2HCl Std. mother solution to 10.0 ml with water.

d. Cysteamine Reference Solution (0.10%) was prepared by dissolving about 100.0 mg of working standard in a 5 ml volumetric flask and taking to volume with water for HPLC. 1.0 ml of this solution was diluted up to 100.0 ml with water; then 1 ml of this last solution was diluted to 10.0 ml with water. (Conc. 0.02 mg/ml).

2,2-Dimethylthiazolidine Assay by Gas Chromatography 2,2-dimethylthiazolidine purity was evaluated by GC according to the following method and conditions:

Capillary column: Ultra 2 or equivalent; Stationary phase: 5% phenyl, 95% dimethyl polysiloxane; Column length 25 m; Column diameter 0.32 mm; Film thickness 0.52 μm; Column temperature: from 50° C. to 280° C. at 10° C./min, 2 minutes at 280° C.; Injector temperature 200° C.; Detector temperature 290° C.; Carrier P helium=50 KPa; Internal Standard Solution: 0.4 ml of toluene taken to 250 ml with methanol; Reference standard solution: 100 mg of 2,2-dimethylthiazolidine taken to 25 ml with the internal std solution; Injection: 0.5 μl.

Water Content

Water content was determined by Karl Fisher's method according to European Pharmacopeia (2.5.12.) on 250.0 mg of product using as reference methanol added with N-ethylmaleimide, in which the water content was previously determined.

X-Ray Powder Diffraction (XRPD): Range 3-40°2Theta; 3-80°2Theta

The X-ray powder diffraction pattern was recorded at room temperature on an X'Pert PRO PANalytical Instrument, Application SW with Cu Kα radiation (λ=1.54060 Å), running at 45 kV and 40 mA, single continuous scan in reflection mode.

To avoid the conversion of the anhydrous crystalline Cysteamine Bitartrate form L2 into the monohydrate form L1, sample preparations and analyses were carried out at temperature not greater than 25° C. and RH % not greater than 25%.

Differential Scanning Calorimetry (DSC): Range 20-350° C., Rate: 10° K/min; Instrument: Mettler Toledo DSC1

Dynamic Vapor Sorption (DVS): Range 0-90% RH, Step: 5% RH, Instrument type: SMS-DVS Intrinsic, Temperature 25° C.

Melting Range

Preheating the instrument (Buchi 545-B or equivalent) to 108° C.; after reaching 113° C., inserting the capillary tube containing the product, then continue increasing the temperature of 1° C./min. up to complete fusion (with decomposition).

Infrared absorption spectrum: Attenuated Total Reflection (ATR) method, Instrument Perkin Elmer Spectrum Two, Range 650-4000 $cm^{-1}$.

Loss on Drying

The loss of weight of the sample was assessed by drying 1.00 g of substance under vacuum at 60° C. for 3 hours, according to the method described in the European Pharmacopeia (2.2.32).

Particle Size Distribution

Particle size distribution was evaluated in line with European Pharmacopeia 2.9.31 with the instrument and according to sample preparation and test conditions reported in the following Table 3:

TABLE 3

| | |
|---|---|
| Instrument | EYE TECH laser particle size analyser |
| Dispersing Agent | Fluid Silicone Oil "200 fluid 20 cs DOW CORNING" index of refraction = 1.403 |
| Operating parameters | acquisition time: 3 minutes<br>lens type: A (0.5-150 μm)<br>sample type: regular<br>cuvette type: magnetic stirred<br>stirring speed: 2 |
| Sample preparation | Suspending about 50 mg of the sample in 5 ml of silicone oil (viscosity 20 CSt ± 2 at 25° C.) and mixing with a vortex mixer for about 30 seconds. Diluting 1 ml of this suspension to 5 ml with the silicone oil and mixing again with vortex. Transferring an aliquot of this preparation to a reading cell with magnetic stirrer and performing the measurement. Measurements were carried out rapidly to avoid settling of the powder. |

$^{1}H$ NMR spectrum: The Nuclear Magnetic Resonance Spectrum of Cysteamine Bitartrate in DMSO was recorded on a Bruker CAB AV4 400 MHZ NMR Spectrometer.

$^{13}C$ NMR spectrum: The NMR $^{13}C$ spectrum of Cysteamine Bitartrate in DMSO was recorded on a Bruker CAB AV4 400 MHZ NMR Spectrometer.

MS spectrum: The Mass spectrum of Cysteamine Bitartrate was performed on a thermo Fisher LCQ-Fleet, using the ESI(+) ionization technique, by dissolving the sample in Methanol.

Bulk density and Tapped density: were measured according to the method of pharmacopoeia (Ph. Eur. 2.9.34). 100 g of sample was weighed and then placed in the test tube, noting the apparent volume without any type of treatment to the sample. Afterwards, 10, 500 and 1250 taps are made using the automatic volumeter (Model: Schleuniger JV2000, Equipment code: CE9), noting the apparent volumes obtained in these three tests. In the event that the difference between the volume obtained for the 500 and 1250 taps was greater than 2 ml, the operation was repeated in increments of 1250 taps until the difference within measurements is less than or equal to 2 ml. For each batch the test was carried out in duplicate.

The bulk density and tapped density were calculated according to the following equations:

Bulk density:

$$\delta 0 = m/V_0 (g/ml)$$

where m is the amount of sample weighed expressed in grams and $V_0$ is the apparent uncompacted volume expressed in milliliters.

Tapped density:

$$\delta = m/V_{1250} (g/ml) \text{ or } \delta = m/V_{2500} (g/ml)$$

where $V_{1250}$ and $V_{2500}$ is the compacted apparent volume at 1250 and 2500 taps.

Optical microscopy: the powders were observed with an Optech SL Dual trinocular stereomicroscope equipped with polarised light, with a camera Optech 318CU 3.2M CMOS (software for pictures: Micrometrics SE Premium). The samples were directly observed under the microscope without further preparation.

Preparation of Cysteamine Bitartrate

Cysteamine Bitartrate was prepared according to the steps reported in the following Scheme 5:

Scheme 5

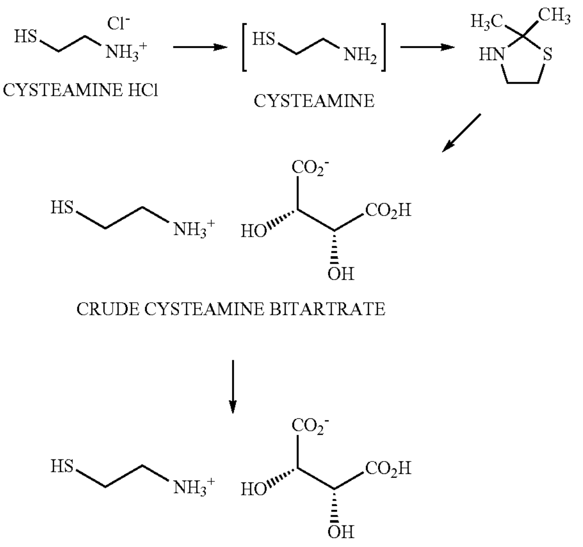

CYSTEAMINE HCl

CYSTEAMINE

CRUDE CYSTEAMINE BITARTRATE

CYSTEAMINE BITARTRATE

Example 1

Preparation and Work-Up of 2,2-dimethylthiazolidine (II)

In this example, Cysteamine Hydrochloride (I—HCl) was reacted with acetone in the presence of sodium hydroxide and sodium thiosulfate to provide 2,2-dimethylthiazolidine (II) as described below.

The starting material Cysteamine Hydrochloride (I—HCl) was prepared according to J. Chem. Soc. C, (1967), 1373-1376 (HPLC purity about 99.0%).

A first reactor (800 l), equipped with a stirrer, reflux condenser and distillation equipment, was charged with purified water (128 l) and sodium thiosulfate pentahydrate (606 g, 2.44 mol) and washed three times with vacuum/nitrogen under stirring.

Cysteamine Hydrochloride (I—HCl, 80 kg, 0.704 Kmol) was added under stirring and the mass was cooled at about 10-15° C. keeping under nitrogen flow.

A solution containing purified water (72 l, 0.9 vol. vs I—HCl), sodium hydroxide (31 Kg, 0.775 Kmol) and sodium thiosulfate pentahydrate (513 g, 2.07 mol) was prepared in a second reactor (500 l) and cooled at about 5-10° C. This solution was then slowly added to the first reactor keeping the temperature between 10 and 23° C.

After stirring for at least 10 minutes, the pH in the first reactor was checked (pH of about 13 by litmus paper) and the solution was cooled at 10-15° C.

Acetone (43 Kg, 0.740 Kmol), pre-cooled at 10-15° C., was added in at least 1 hour, keeping under stirring at 14-18° C. for other 2 hours.

Sodium chloride (3.8 Kg, 0.065 Kmol) and cyclohexane (237 Kg, 3.8 vol. vs I—HCl) were then charged in the first reactor, keeping under stirring at 14-18° C. for 15 minutes and then letting it stands for 20 minutes.

The aqueous phase was unloaded and the organic cyclohexane phase containing the product was sent into a third reactor, added with anhydrous sodium sulphate (1.6 Kg, 0.011 Kmol), kept under stirring at 15-20° C. for at least 1 hour and then filtered over a filter charged with 6.4 Kg of anhydrous Sodium Sulphate.

The filter was washed with cyclohexane (13 Kg). The combined dried organic phases were distilled under vacuum at a pressure decreasing from 250 to 80 mbar, without exceeding 50° C. to minimize product loss through evaporation. The distillation residue, containing 2,2-dimethylthiazolidine in cyclohexane, was added with acetone (34 l) and distilled again under the same conditions.

Removal of the acetone/cyclohexane admixture provided a residue of 2,2-dimethylthiazolidine (II) as a colourless liquid (yield: 74%, 60.7 kg at 100%).

Analysis: IR spectrum is equivalent to the reference standard spectrum; GC purity 98.5%.

Example 2

Preparation of Crude Cysteamine Bitartrate (I) from 2,2-dimethylthiazolidine (II)

85.7 Kg of L (+)-Tartaric acid (0.57 Kmol) and 120 l purified water were charged into a first reactor and stirred under nitrogen up to complete dissolution. After three washes with vacuum/nitrogen, crude 2,2 dimethylthiazolidine (II) (60.7 Kg at 100%, 0.518 Kmol) prepared according to Example 1 was added to the solution. The aqueous mass was heated at 48-52° C. and kept under these conditions, for at least three hours.

The acetone formed as reaction by-product was removed by distillation under vacuum without exceeding 50° C. in the next steps. First, 36 I of the solvent admixture was distilled off then the reactor was loaded with purified water (34 l).

The treatment was then repeated up to complete removal of acetone, each time distilling about 21 l of solvent admixture and replenishing with 17 l of water.

In a second reactor, 2-propanol (364 l) and crystalline anhydrous Cysteamine Bitartrate (I) (polymorph L2) (10 g) as seeding were charged then degassed with vacuum/nitrogen cycles.

The Cysteamine Bitartrate aqueous solution, previously prepared in the first reactor, was then transferred into the second reactor, in at least 1 hour and under stirring, keeping temperature between 20 and 35° C.

The first reactor was washed with 8.6 l of water and the washing sent to the second reactor.

The mass in the second reactor was stirred for at least 30 minutes at 30-35° C. and then cooled at 18-22° C. in about 2 hours. It was then kept under stirring at 18-22° C. for at least 16 hours. The slurry was centrifuged and washed twice with a mixture of 15 l of water and 45 I of 2-propanol.

The cake was unloaded obtaining wet Crude Cysteamine Bitartrate, A sample of the wet Crude Cysteamine Bitartrate was dried at 30° C. overnight under vacuum (about 3 mbar) and subjected to XRPD analysis, resulting to be the crude monohydrate Cysteamine Bitartrate (polymorph L1). The remaining cake was dried under vacuum at 40+60° C. up to a final water content lower than 2% ww, thus providing crude anhydrous Cysteamine Bitartrate polymorph L2 (XRPD analysis). 102 Kg of crude Cysteamine Bitartrate were obtained after drying at 40-60° C. with a yield of about 87% mol vs 2,2-dimethylthiazolidine 100%.

Analysis: Crude Cysteamine Bitartrate was characterized as shown in the Table 4 below:

TABLE 4

| | Crude Cysteamine Bitartrate Ex. 2 |
|---|---|
| Appearance | White powder |
| Identification (IR) | Compliant with reference |
| K.F. | 0.85% |
| pH[1] | 3.53 |
| HPLC purity (area %) | |
| Cysteamine Bitartrate | 99.90% |
| Cystamine | 0.04% |
| 2,2-DMT | 0.01% |
| Total. Imp. | 0.08% |
| Residual solvents | |
| Acetone | ≤18 ppm |
| 2-Propanol | ≤60 ppm |
| c-Hexane | ≤10 ppm |
| Yield (mol %) | 86.9% |
| XRPD | (dried at 30° C.) L1 |
| (Main crystalline Form) | (dried at 40-60° C.) L2 |

Keys: [1] pH was determined potentiometrically on a solution of 100 mg of sample dissolved in 10 ml of water; HPLC purity is expressed as area percentage (area of the peak/total area×100); DMT: 2,2-dimethylthiazolidine.

As can be seen from Table 4, the crude Cysteamine Bitartrate already had high HPLC purity with a low content of Cystamine (0.04%).

The main crystalline form observed in the diffractogram of crude Cysteamine Bitartrate, after drying at 40-60° C., corresponded to Form L2.

Example 3: Crystallization Tests

A few Cysteamine Bitartrate crystallization tests were performed on approximately 100 g of product using the following solvents and conditions:

Ex. 3a: Cysteamine Bitartrate salt was dissolved in water and EtOH was dropwise added, as anti-solvent, to the aqueous solution of Cysteamine Bitartrate. Poor yields were obtained due to the high solubility of the product in the water—EtOH crystallization admixture.

Ex. 3b—Cysteamine Bitartrate salt was dissolved in water and 2-propanol was added dropwise, as anti-solvent, to the aqueous solution of Cysteamine Bitartrate. A sticky solid difficult to handle was obtained.

Ex. 3c—Cysteamine Bitartrate salt was dissolved in 1 volume of water at about 50° C.; then the concentrated solution was dropped over a solution of 2-propanol and water at room temperature in about one hour under vigorous stirring. The product started to precipitate immediately.

Once dropping had been completed, the suspension under stirring was warmed to 30-35° C. to improve and homogenize the crystalline form, cooled and further kept at 20° C. under stirring, thus providing a crystalline form that was easy filtered and washed.

Example 4

Scale-Up Preparation of Crystalline Anhydrous Cysteamine Bitartrate (polymorph L2) by Crystallization from 2-Propanol-Water (Inverse Addition)

A glass lined reactor (500 l) equipped with stirrer, reflux condenser and distillation equipment, was charged with crude Cysteamine Bitartrate (100 kg, 0.44 Kmol), prepared according to Example 2, and with purified water (100 l). The reactor was washed three times with vacuum/nitrogen and then the mass was heated to 48-52° C. under stirring for at least 30 minutes up to complete dissolution.

A second reactor was charged with 2-propanol (525 l), purified water (50 l) and anhydrous crystalline Cysteamine Bitartrate (polymorph L2) (10 g) as seeding, washed three times with vacuum/nitrogen and then the mass was heated to 20-35° C.

The solution of the first reactor was transferred into the second reactor in at least 1 hour under stirring, keeping the temperature between 20 and 35° C. The first reactor was washed with 10 l of purified water, which was then added to the mass in the second reactor.

The mass in the second reactor was stirred for at least 30 minutes at 30-35° C., cooled at 18-22° C. in about 2 hours and then kept under stirring at 18-22° C. for at least 16 hours.

The slurry was centrifuged and washed twice with a mixture of 15 l of purified water and 45 l of 2-propanol.

The cake was unloaded thus obtaining wet Cysteamine Bitartrate (100 kg).

Wet Cysteamine Bitartrate was charged into a drier and dried under vacuum at 40-60° C. at about 25 mbar up to a water content lower than 0.5% ww, and finally sieved with a sieve having openings of 600 microns, thus providing 72.5 Kg of anhydrous crystalline Cysteamine Bitartrate (yield from DMT up to anhydrous crystalline Cysteamine Bitartrate: 62% mol; crystallization yield: 78.9% mol) The final properties of the product are summarized in Table 5 below:

TABLE 5

| | Anhydrous crystalline Cysteamine Bitartrate (Ex. 4) |
|---|---|
| Appearance | White powder |
| m.p. (° C.) | 120.3 |
| Identification (IR) | Compliant with reference |
| Loss on drying (60° C., 3 h) | 0.20% |
| K.F. | 0.06% |
| HPLC purity (Area %) | |
| Cysteamine Bitartrate | 99.97% |
| Cystamine | <0.05% |
| 2,2-DMT | <0.05% |
| Tot. imp. | <0.05% |
| Residual solvents | |
| Acetone | <60 ppm |
| 2-Propanol | <60 ppm |
| c-Hexane | n.a. |
| Average particle size by volume D50, D90 (media on 3 batches) | D50: 28.4 μm<br>D90: 102.5 μm |

n.a.: not assessed

The anhydrous crystalline Cysteamine Bitartrate prepared as described above in Example 4 was further analysed by XRPD, DSC, DVS, $^{1}$H-NMR, $^{13}$C-NMR, IR and mass analysis (See FIG. 1 to 9).

Thermal analysis by DSC showed endothermic transitions at about 56, 121, 160 and 190° C. attributed to small water loss, melting and, above (140° C., subsequent decomposition as disclosed in FIG. 2.

XRPD analysis showed no significant differences in comparison to the XRPD spectrum of Form L2 published in U.S. Ser. No. 10/251,850, as appears from the spectrum in FIG. 1.

The chemical shifts and spectral assignments of the protons in the H-NMR spectrum, 400 MHz in DMSO-d6, are reported in Table 6 below:

TABLE 6

| Assignments | Chemical Shift (ppm) | N. of hydrogens |
|---|---|---|
| —CH2—SH Cysteamine | 2.69-2.71 | 2H (t) |
| —CH2—NH3+ Cysteamine | 2.94-2.96 | 2H (t) |
| —CHOH—CHOH— tartaric acid | 4.00 | 2H (d) |
| NH2, SH Cysteamine<br>2x COOH, 2x OH, tartaric acid | 7.10 | 7H (bs) |

The $^{1}$H-NMR spectrum of anhydrous crystalline Cysteamine Bitartrate obtained with the process of the present invention is shown in FIG. 4.

The chemical shifts and spectral assignments of the carbons in the $^{13}$C-NMR spectrum, at 100 MHz in DMSO-d6, are reported in Table 7 below:

TABLE 7

| Assignments | Chemical Shift (ppm) |
|---|---|
| —CH2—SH Cysteamine | 21.48 |
| DMSO | 37.97-40.14 |
| —CH2—NH3+ Cysteamine | 41.9 |
| 2x —CHOH— tartaric acid | 72.15 |
| 2x HOOC— tartaric acid | 174.83 |

The $^{13}$C-NMR spectrum of anhydrous crystalline Cysteamine Bitartrate obtained with the process of the present invention is shown in FIG. 5.

The Infrared Absorption Spectrum of anhydrous crystalline Cysteamine Bitartrate obtained with the process of the present invention exhibits maxima as shown in FIG. 6.

The full scan mass spectrum, range 50-300 m/z, of anhydrous crystalline Cysteamine Bitartrate obtained with the process of the present invention shows the quasi-molecular ion [M+H]+ of Cysteamine with 78 m/z.

The mass spectrum of anhydrous crystalline Cysteamine Bitartrate obtained with the process of the present invention is shown in FIG. 7.

DVS Analysis 0%-90%, Step 5%

A DVS analysis was performed on a sample of anhydrous Cysteamine Bitartrate prepared according to Example 4 to evaluate at which RH % the conversion into the hydrate form started. FIG. 3 shows the plot of water sorption isotherm. It can be see that the hydration process started at 25% RH and finished at 35% RH and that during this process the sample gained 7.5% w/w of water (compatible with 1 mol of water). The XRPD analysis performed on the sample after the DVS analysis confirmed that it had converted into the hydrate form.

Example 5: Stability Tests

Cysteamine Bitartrate batches (3 batches for test) prepared according to Example 4 were subjected to stability tests as described below.

Long Term Stability:

Stability samples were stored under controlled conditions at 25±2° C. and 60±5% R. H., packed in the same type of containers as for shipping, according to the current ICH guidelines on stability.

At intervals of 6 months, volumetric assay (on anhydrous or on dried basis), HPLC related substances and loss on drying or water content by Karl-Fischer were assessed on 3 batches, according to the methods previously reported and with the results shown in Tables 8A-8C below:

TABLE 8A

| Test | Acceptance criteria | Months 0 | 6 | 12 | 18 | 24 | 36 |
|---|---|---|---|---|---|---|---|
| Volumetric Assay (on dried basis) % | 98.0 to 102.0% | 99.8 | 99.6 | 99.9 | 99.8 | 99.8 | — |
| Volumetric Assay (on anhydrous) % | 98.0 to 102.0% | — | — | — | — | — | 100.5 |
| HPLC Related Substances % | Cystamine: NMT 1.0% | 0.08 | 0.10 | 0.11 | 0.12 | 0.13 | |
| | 2,2-dimethylthiazolidine: NMT 0.10% | <0.02 | <0.02 | <0.02 | <0.02 | <0.02 | |
| | Di-Cysteamine acetonide: NMT 0.10% | <0.02 | <0.02 | <0.02 | <0.02 | <0.02 | |
| | Other impurities: NMT 0.10% | <0.002 | <0.02 | <0.02 | <0.02 | <0.02 | |
| | Total of impurities: NMT 1.5% | 0.08 | 0.10 | 0.11 | 0.12 | 0.13 | |
| Loss on drying | NMT 1.0% | 0.04 | 0.07 | 0.20 | 0.14 | 0.30 | |
| Water Content (K.F.) % | NMT 1.0% | — | — | — | — | — | 0.81 |

NMT: no more than

TABLE 8B

| Test | Acceptance criteria | Months 0 | 6 | 12 | 18 | 24 | 36 |
|---|---|---|---|---|---|---|---|
| Volumetric Assay (on dried basis) % | 98.0 to 102.0% | 100.2 | 99.6 | 99.4 | 100.0 | 99.6 | — |
| Volumetric Assay (on anhydrous) % | 98.0 to 102.0% | — | — | — | — | — | 100.2 |
| HPLC Related Substances % | Cystamine: NMT 1.0% | 0.05 | 0.09 | 0.09 | 0.11 | 0.12 | |
| | 2,2-dimethylthiazolidine: NMT 0.10% | <0.02 | <0.02 | <0.02 | <0.02 | <0.02 | |
| | Di-Cysteamine acetonide: NMT 0.10% | <0.02 | <0.02 | <0.02 | <0.02 | 0.02 | |
| | Other impurities: NMT 0.10% | <0.05 | <0.02 | <0.02 | <0.02 | <0.02 | |
| | Total of impurities: NMT 1.5% | 0.05 | 0.09 | 0.09 | 0.11 | 0.12 | |
| Loss on drying | NMT 1.0% | 0.15 | 0.15 | 0.25 | 0.07 | 0.27 | |
| Water Content (K.F.) % | NMT 1.0% | — | — | — | — | — | 0.47 |

TABLE 8C

| Test | Acceptance criteria | Months 0 | 6 | 12 | 18 | 24 | 36 |
|---|---|---|---|---|---|---|---|
| Volumetric Assay (on dried basis) % | 98.0 to 102.0% | 99.7 | 99.9 | 99.5 | 99.7 | 99.7 | — |
| Volumetric Assay (on anhydrous) % | 98.0 to 102.0% | — | — | — | — | — | 100.4 |
| HPLC Related Substances % | Cystamine: NMT 1.0% | 0.09 | 0.10 | 0.11 | 0.12 | 0.12 | |
| | 2,2-dimethylthiazolidine: NMT 0.10% | <0.02 | <0.02 | <0.02 | <0.02 | <0.02 | |
| | Di-Cysteamine acetonide: NMT 0.10% | <0.02 | <0.02 | <0.02 | <0.02 | <0.02 | |
| | Other impurities: NMT 0.10% | <0.02 | <0.02 | <0.02 | <0.02 | <0.02 | |
| | Total of impurities: NMT 1.5% | 0.09 | 0.10 | 0.11 | 0.12 | 0.12 | |
| Loss on drying | NMT 1.0% | 0.23 | 0.14 | 0.19 | 0.07 | 0.38 | |
| Water Content (K.F.) % | NMT 1.0% | — | — | — | — | — | 0.67 |

The long-term stability data reported above according to the ICH guidelines on stability, show that no significant degradation occurs after 36 months.

Accelerated Stability Studies:

Stability samples are stored in controlled conditions at 40±2° C. and 75±5% R. H., packed in the same type of containers as for shipping, according to the current ICH guidelines on stability.

At intervals of 3 months, volumetric assay, HPLC related substances and loss on drying were assessed on 3 batches, according to the methods previously reported and with the results shown in Tables 9A-9C below:

TABLE 9A

| Test | Acceptance criteria | Months 0 | 3 | 6 |
|---|---|---|---|---|
| Volumetric Assay (on anhydrous) % | 98.0 to 102.0% | 99.8 | 99.5 | 99.8 |
| HPLC Related Substances % | Cystamine: NMT 1.0% | 0.08 | 0.14 | 0.20 |
| | 2,2-dimethylthiazolidine: NMT 0.10% | <0.02 | <0.02 | <0.02 |
| | Di-Cysteamine acetonide: NMT 0.10% | <0.02 | <0.02 | <0.02 |
| | Other impurities: NMT 0.10% | <0.02 | <0.05 | <0.05 |
| | Total of impurities: NMT 1.5% | 0.08 | 0.14 | 0.20 |
| Loss on drying | NMT 1.0% | 0.04 | 0.04 | 0.13 |

TABLE 9B

| Test | Acceptance criteria | Months 0 | 3 | 6 |
|---|---|---|---|---|
| Volumetric Assay (on anhydrous) % | 98.0 to 102.0% | 100.2 | 99.4 | 99.7 |
| HPLC Related | Cystamine: NMT 1.0% | 0.05 | 0.11 | 0.10 |

TABLE 9B-continued

| Test | Acceptance criteria | Months 0 | 3 | 6 |
|---|---|---|---|---|
| Substances % | 2,2-dimethylthiazolidine: NMT 0.10% | <0.02 | <0.02 | <0.02 |
| | Di-Cysteamine acetonide: NMT 0.10% | <0.02 | <0.02 | <0.02 |
| | Other impurities: NMT 0.10% | <0.05 | <0.05 | <0.02 |
| | Total of impurities: NMT 1.5% | 0.05 | 0.11 | 0.10 |
| Loss on drying | NMT 1.0% | 0.15 | 0.03 | 0.09 |

TABLE 9C

| Test | Acceptance criteria | Months 0 | 3 | 6 |
|---|---|---|---|---|
| Volumetric Assay (on anhydrous) % | 98.0 to 102.0% | 100.2 | 99.4 | 99.6 |
| HPLC Related Substances % | Cystamine: NMT 1.0% | 0.09 | 0.09 | 0.13 |
| | 2,2-dimethylthiazolidine: NMT 0.10% | <0.02 | <0.02 | <0.02 |
| | Di-Cysteamine acetonide: NMT 0.10% | <0.02 | <0.02 | <0.02 |
| | Other impurities: NMT 0.10% | <0.02 | <0.02 | <0.05 |
| | Total of impurities: NMT 1.5% | 0.09 | 0.09 | 0.13 |
| Loss on drying | NMT 1.0% | 0.23 | 0.02 | 0.04 |

The accelerated stability data reported above according to the ICH guidelines on stability, show that no significant degradation occurs after 6 months.

Example 6: Comparison of Anhydrous Crystalline Cysteamine Bitartrate, Prepared According to the Present Invention, with a Commercial Cysteamine Bitartrate In the present study, three batches of anhydrous crystalline Cysteamine Bitartrate (Recordati R1-R3), prepared according to Example 4, were analysed in comparison with three batches of a commercial Cysteamine Bitartrate (comparison C1-C3).

The commercial Cysteamine Bitartrate was crystallized from ethanol.

The approved specifications, the analyses and the results for the batches according to the invention and for the comparative batches are summarized in the following Table 10:

TABLE 10

| Test | Specifications | C1 | C2 | C3 | R1 | R2 | R3 |
|---|---|---|---|---|---|---|---|
| Appearance | White crystalline powder | OK | OK | OK | OK | OK | OK |
| Identification | IR spectrum vs std reference spectrum | OK | OK | OK | OK | OK | OK |
| Melting range | 118° C. to 121° C. | 117.3 | 117.7 | 117.1 | 120.0 | 120.2 | 120.1 |
| Appearance of solution§ | Clear | OK | OK | OK | OK | OK | OK |
| Assay Cysteamine (on dry basis) | Between 97.0% and 102.0% | 95.5% | 95.7% | 95.9% | 99.7% | 99.5% | 99.3% |
| Free Tartaric Acid assay | Not more than 1.0% | 1.6% | 1.3% | 1.0% | 0.3% | <0.1% (N.D.) | <0.1% (N.D.) |
| Cystamine assay | Not more than 2.0% | 4.2% | 3.9% | 3.9% | <0.1% | 0.1% | 0.2% |
| Particle Size | D50 <150 mic | ~65% | ~55% | ~53% | OK (100%) | OK (100%) | OK (100%) |
| Particle Size | D90 <450 mic | OK (100%) | OK (100%) | OK (100%) | OK (100%) | OK (100%) | OK (100%) |

Keys: OK means complies; N.D.: not detectable; § 2% water solution (500 mg of sample in 25 ml of water).

As can be appreciated from Table 10 above, the three batches R1-R3 of Cysteamine Bitartrate according to the invention resulted always compliant to the specifications while the comparative samples C1-C3 gave out of specifications results for melting point, assay (on dry basis), Cystamine and free tartaric acid content.

Regarding the PSD, the commercial batches complied only partially with the requirement of D50<150 microns while the batches according to the invention were always in line with all the PSD specifications.

In conclusion, compared to the commercial comparison product, the Cysteamine Bitartrate of the invention has a higher HPLC purity, longer stability (at least up to 36 months) and, unlike the commercial comparison batches, a particle size distribution that is 100% compliant with the specifications.

The anhydrous crystalline Cysteamine Bitartrate of the present invention, thanks to the high purity and to the particular small size of the particles that could make unnecessary further micronization steps, was particularly stable and, if stored in closed dark containers under inert gasses, could keep the characterizing analytical parameters unaltered and be compliant with the approved standard regulatory requirements up to 36 months and even longer.

Example 7: Preparation of Crude Cysteamine Bitartrate According to IN202041000697A (Comparison Example)

Crude monohydrate Cysteamine Bitartrate (I) was prepared according to the process described under Examples 7 to 9 of the Indian patent application IN202041000697A.

Example 7A: Preparation of 2-Aminoethyl Hydrogensulfate (Ex. 7 of IN202041000697A)

Scheme 6

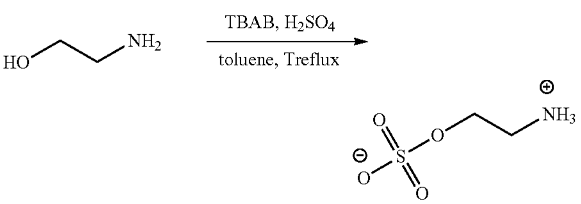

Sulfuric acid (1.1 eq., 96.5 ml) was slowly added to the pre-cooled mixture of toluene (6 vol., 600 ml), ethanolamine (100 g), tetra-n-butylammonium bromide (0.19 eq. 100 g) at 10-15° C., the admixture was stirred for 15 minutes at 25-30° C. then heated overnight under stirring at reflux temperature. The reaction mixture was cooled at 25-30° C., 2-propanol was added at 25-30° C. (4 vol.) and stirred. The precipitated solid was filtered, washed with 2-propanol (1 vol.), slurried in 2-propanol (5 vol.) at r.t. for 2 hours and finally filtered to get the titled compound (Yield 92%). $^{1}$H-NMR detected the titled compound only.

Example 7B: Preparation of 2-ethyl-2-methylthiazolidine (Ex. 8 of IN202041000697A)

Scheme 7

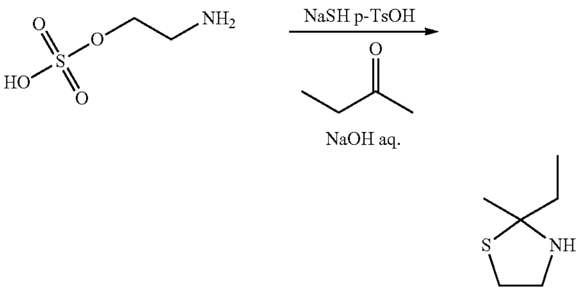

(II)

Sodium hydroxide (1.0 eq., 76.0 g) was added under stirring to the mixture of 2-aminoethyl hydrogensulfate obtained in Example 7A (268 g), aqueous sodium hydrosulfide (2.0 eq. 213 g, in 4 vol. of water), methyl ethyl ketone (4 eq., 680 ml) at 25-30° C. Para-toluene sulfonic acid monohydrate (0.1 eq.) was added at 25-30° C., then the admixture was heated to 80-85° C. and kept under stirring overnight at the same temperature. The admixture was then cooled at 25-30° C., stirred, filtered and washed with methyl ethyl ketone. The organic layer was separated and the aqueous phase was extracted with methyl ethyl ketone. The combined organic layers were washed with aqueous sodium hydroxide solution then with aqueous sodium chloride. Finally, the solvent of the organic layers was completely distilled off to get the title compound (Yield 60%). $^1$H-NMR on the final compound detected 5% w/w of MEK.

By comparing the outcome of this process for the manufacture of the 2,2-disubstituted thiazolidine with the one according to the invention of Example 1, carried out under very basic conditions and with Cysteamine as starting material instead of 2-aminoethyl hydrogensulfate, it is evident that the process of the invention, is advantageous both in terms of yields and of purity (Yields: 74% vs 60%; GC purity: 98% vs 93%).

Example 7C: Preparation of Crude monohydrate Cysteamine Bitartrate (Ex. 9 of IN202041000697A)

2-methyl 2-ethylthiazolidine (1 eq. 100 g), prepared in Example 7B, was added in 30 min at 25-30° C. to the solution of L-(+)-tartaic acid (1.1 eq, 126 g) in 2-propanol (11.2 vol., 1120 ml) and water (2.2 vol., 220 ml) prepared at 25-30° C. under nitrogen and stirred at the same temperature. The admixture was stirred overnight, the precipitated solid was filtered, washed with 2-propanol (1 vol., 100 ml) and dried overnight under vacuum (about 3 mbar) at 30° C. (HPLC purity 95.5%) (Yield: 70%).

Example 8: Preparation of Crude Cysteamine Bitartrate According to IN202041000697A (Example 9) but using of 2,2-dimethylthiazolidine (DMT) instead of 2-methyl-2-ethyl thiazolidine (MET) as starting material.

Crude Cysteamine Bitartrate was prepared by following the same procedure of Example 7C but starting from 100 g of 2,2-dimethylthiazolidine (DMT) prepared according to Example 1. The final crude Cysteamine Bitartrate showed HPLC purity of 98.5% (Yield: 85%).

Example 9: Preparation of Crude Cysteamine Bitartrate According to the Present Invention but using 2-methyl-2-ethyl thiazolidine (MET) from Ex. 7B as starting material.

Crude Cysteamine Bitartrate was prepared by following the same procedure of Example 2 but starting from 2-methyl-2-ethyl thiazolidine (MET) prepared according to Example 7B. The final crude Cysteamine Bitartrate showed HPLC purity of 95.6% (Yield: 65%).

Both the crude Cysteamine Bitartrate obtained according to Example 7C and to Example 9 contained Cystamine (RRT 3.3, HPLC % 3.9-4.0).

As Cystamine resulted difficult to be remove by crystallization from water/2-propanol (see Table 12), it was important to avoid or minimize its presence in the crude Cysteamine Bitartrate, for instance by using as thiazolidine the present DMT instead of MET of Example 7B.

The results of the above experiments are summarized in the following Table 11:

TABLE 11

| | THIAZ | reaction with TA (step b) and precipitation of crude CB (steps h1-h2) | THIAZ GC Purity | crude CB HPLC purity | crude CB Yield % mol |
|---|---|---|---|---|---|
| Ex. 2 (INV) | DMT (Ex. 1 INV) | See Example 2 (INV) | 98% | 99.9% (Cystamine 0.04%) (DMT 0.01%) | 87% |
| Ex. 7C (COMP) | MET (Ex. 7B COMP) | See Example 7C (COMP) | 93% | 95.5% (Cystamine 3.9%) | 70% |
| Ex. 8 (COMP) | DMT (Ex. 1 INV) | See Example 7C (COMP) | 98% | 98.6% (DMT 0.45%; Cystamine 0.82%) | 85% |
| Ex. 9 (COMP) | MET (Ex. 7B COMP) | See Example 2 (INV) | 93% | 95.6% (Cystamine 4.0%) | 65% |

Keys: THIAZ: thiazolidine; TA: tartaric acid; DMT: 2,2-dimethylthiazolidine; MET: 2,2-methyl ethyl-thiazolidine; INV: invention; COMP: comparative; CB Cysteamine Bitartrate; Cystamine (RRT 3.3 min); n.d.: not detectable.

According to the data reported above, the process for the preparation of the crude Cysteamine Bitartrate according to the invention (Example 2) provided the best yields and purity.

In particular, by comparing the results of Example 7C and Example 8, it appeared that the chemical purity of the crude Cysteamine Bitartrate obtained by using as starting material MET prepared according to prior art was clearly lower (HPLC purity about 95.5%) than that of the product obtained with the same process but starting from the present DMT (HPLC purity 98.5%). The yield of crude Cysteamine Bitartrate also increased from 70% to 85% in respect of prior art teaching.

Instead, by comparing the results of Example 7C and Example 9 it appeared that the chemical purity and the yield of the crude Cysteamine Bitartrate obtained starting from the same prior art MET were comparable for the processes.

By comparing the analyses on the product obtained according to the process of Example 8 (Comparative) with those of the product from Example 2 (Invention), both processes starting from the same DMT but applying different reaction and isolation conditions, it appeared that the process of the invention provided for a purer crude Cysteamine Bitartrate (99, 90% vs 98.6%) with a lower content of Cystamine (0.04% vs 0.82%) with a slight yield increase (87% vs 85%). In addition, the process of the invention provided for a substantially complete conversion of the starting DMT (residual DMT 0.01% vs 0.45%).

Finally, by comparing the whole processes (from the respective thiazolidine, including the reaction with tartaric acid and the following Cysteamine Bitartrate crude precipitation) of Example 7C (IN202041000697A) and of Example 2 (present invention) it appeared that a significant increase in yields and purity was obtained with the present invention (yield from 70% to about 87%; HPLC purity from 95.5% to 99.9%).

In conclusion, in view of the data reported in Table 11 above, it appeared that the process according to the present invention provided crude Cysteamine Bitartrate with higher yields and purity in comparison with the process described in IN202041000697A.

Example 10: Crystallization of Crude Cysteamine Bitartrate (Invention vs IN202041000697A)

Crude Cysteamine Bitartrate was prepared according to Example 2. Samples from the same batch were subjected to different crystallization conditions from water/2-propanol, as detailed in the following examples.

Example 10A: Crystallization of Crude Cysteamine Bitartrate by Inverse Addition (Invention)

Crude Cysteamine Bitartrate (100 g) was crystallized as described in Example 4 (inverse addition, namely Cysteine Bitartrate aqueous solution dropped into 2-propanol seeded with anhydrous Cysteamine Bitartrate Form 12). The cake of Cysteamine Bitartrate was dried overnight under vacuum (about 3 mbar) at 50° C. providing 86 g of Cysteamine Bitartrate.

Yield: 86%; purity by HPLC: 99.6% XRPD: anhydrous Form L2

Example 10B: Crystallization of Crude Cysteamine Bitartrate by Direct Addition (Comparison, Ex. 10 of IN202041000697A)

L(+)-Tartaric acid (0.1 eq. 6.6 g) was added to nitrogen gas purged water (2 vol., 200 ml) at 25-30° C. and stirred under nitrogen atmosphere. Cysteamine Bitartrate (0.1 eq., 100 g) was added and stirred up to dissolution. The solution was filtered and then 2-propanol (9.5 vol., 950 ml) was added to the aqueous solution in 1 hour at room temperature. The admixture was cooled at 7-10° C., stirred, at the same temperature for 2 hours, then the precipitated solid was filtered, washed with 2-propanol (1 vol., 100 ml) and dried overnight under vacuum (about 3 mbar) at 30° C., then at 50° C. up to steady weight providing 91 g of Cysteamine Bitartrate.

Yield: 91%; purity by HPLC: 99.4% (solid dried at 30° C.), 99.3% (solid dried at 50° C.) XRPD: form L1 monohydrate (solid dried at 30° C., called "Form M") (see FIG. 8), form L2 anhydrous (solid dried at 50° C.).

The relevant analytical data (average of analyses on three samples) measured on the crude Cysteamine Bitartrate and on the crystallized Cysteamine Bitartrate of Example 10A and 10B, after drying under vacuum overnight at the reported temperatures, are shown in the following Table 12:

TABLE 12

| | Crude CB | Crystallized CB Ex. 10A (INV) (inverse addition) | Crystallized CB Ex. 10B (COMP) (direct addition) |
|---|---|---|---|
| After drying under vacuum overnight at | | 50° C. | 30° C. then 50° C. |
| HPLC purity | 98.8% | 99.6% | 99.3% |
| Cystamine (RRT 3.3) | 0.58% | 0.39% | 0.52% |
| Crystalline form | Mainly L1 | L2 | L1 (dried at 30° C.), L2 (dried at 50° C.) |
| Powder appearance | — | Compact | Fluffy |
| Bulk density (g/ml) | — | 0.301 | 0.279 |
| Tapped density (g/ml) | — | 0.423 | 0.442 |
| Hausner Ratio | — | 1.41 | 1.58 |

Keys: CB Cysteamine Bitartrate.

From the data reported above, it appeared that the method according to the invention (inverse addition) provided for a slightly purer CB and was more effective in removing Cystamine than the prior art method (direct addition).

Furthermore, the bulk density of the solid obtained by indirect addition according to the invention was clearly higher than that of the solid prepared by direct addition according to prior art. As bulk density is usually a good indicator of the flowability of a powder—with low values indicating poor flow and vice-versa—it followed that the flowability of the powder of the invention is predictively higher than that of prior art powder. This property is known to be advantageous from the pharmaceutical formulation point of view.

Figure 9:
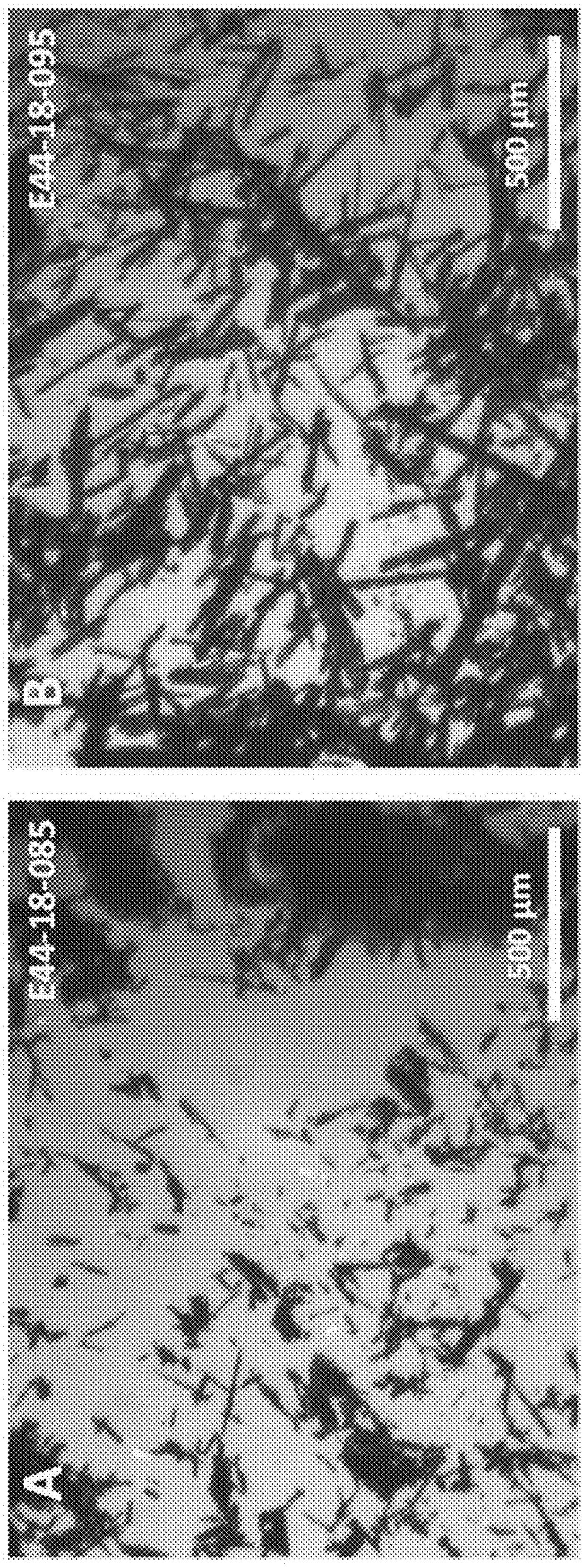
FIG. 9 discloses optical microscopy images of: A) Cysteamine Bitartrate powder of Ex. 10A prepared according to the invention (E44-18-085) and B) Cysteamine Bitartrate powder of Ex. 10B prepared according to prior art (E44-18-095).

The powders recovered from Ex. 10A and 10B were observed by optical microscopy too (FIG. 9). Very elongated prisms tending to an acicular morphology (i.e. needle-like crystals) were observed in both cases. Big needle-like crystals can be undesirable in the pharmaceutical industry, as they can exhibit poor flow properties complicating operations, such as filtration, drying and blending (Crystals 2020, 10, 925). The elongated particles interlock with each other possibly increasing the cohesive strength and hence resist the powder flow.

However, as appeared from FIG. 9, the dimensions of the crystals of the anhydrous Cysteamine Bitartrate (I) (polymorph L2) powder according to the invention (Ex. 10A, FIG. 9A) were much smaller than that of prior art (Ex. 10B, FIG. 9B). The large elongated crystals of prior art powder were responsible for the low bulk density described above and predictive of worse flowability.

Another parameter relevant for evaluating powder flowability is the Hausner ratio namely the ratio between tapped and bulk densities. Generally, a Hausner ratio of higher than 1.50 indicates a very poor flowability (Powder properties in food production systems, Handbook of Food Powders, Ed.: Bhesh Bhandari, Nidhi Bansal, Min Zhang, Pierre Schuck, Woodhead Publishing, 2013, chapter 12, page 298).

From the values of Hausner Ratio reported in Table 12 above, it appeared that Cysteamine Bitartrate crystals in the form obtained according to the invention had better flowability than prior art powder (Hausner ratio 1.41 vs 1.58).

In conclusion, in view of the above, Cysteamine Bitartrate crystallized according to the prior art process (direct addition) showed worse properties if compared to the Cysteamine Bitartrate crystallized according to the process of the present invention, in particular

- a slightly lower chemical purity (99.3 vs. 99.6% a/a HPLC)
- a higher content of Cystamine (0.52% vs 0.39%)
- a lower bulk density (0.279 vs. 0.301 g/mL)
- a higher Hausner ratio (1.58 vs 1.41), predictive of a worse flowability.

The invention claimed is:

1. A process for the manufacture of crude cysteamine bitartrate of formula (I)

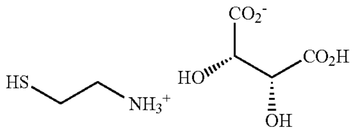

(I)

which comprises:

a) reacting a thiazolidine of formula (II):

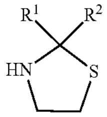

(II)

in which R1 and R2 are each independently selected from H, linear or branched $C_1$-$C_{20}$ alkyl, optionally substituted $C_6$-$C_{20}$ aryl and optionally substituted heteroaryl with L(+)-tartaric acid in an aqueous medium, to obtain crude cysteamine bitartrate (I) in the aqueous medium, and b) isolating said crude cysteamine bitartrate (I) from the aqueous medium, wherein the thiazolidine of formula (II) is prepared according to a one-pot process which comprises:

c) contacting a cysteamine salt with a base in an aqueous medium at a pH of not less than 10.5, to obtain cysteamine free base of formula (I-B)

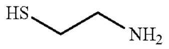

(I-B)

d) reacting the cysteamine free base (I-B) in the same aqueous medium, with a compound of formula (III)

R1-CO—R2 (III)

in which R1 and R2 have the meanings reported above, to obtain the crude thiazolidine (II) and, optionally, e) purifying the thiazolidine of formula (II).

2. The process of claim 1 further comprising, after a), g) precipitating crude cysteamine bitartrate (I) by pouring the aqueous medium from a) into 2-propanol and then b) isolating the precipitated crude wet cysteamine bitartrate (I) from the aqueous medium.

3. The process of claim 2 further comprising, after b), h) drying the precipitated crude wet cysteamine bitartrate (I), to obtain crude cysteamine bitartrate (I).

4. The process of claim 1 wherein the pH of the aqueous medium in c) is not less than 11.

5. The process of claim 1, wherein in the thiazolidine of formula (II) R1 and R2 are the same or different and are selected from H, $C_1$-$C_3$ alkyl and $C_6$-$C_{10}$ aryl, or the thiazolidine of formula (II) and the L(+) tartaric acid are reacted in a) in a molar ratio from 1:1 to 1:2, or the thiazolidine of formula (II) and the L(+) tartaric acid are reacted in a) at a temperature from 45° C. to 55° C., or the reaction of a) is brought to completeness by removing a compound of formula (III) $R^1$—CO—$R^2$ by distillation, or the crude cysteamine bitartrate is isolated from the aqueous reaction medium from a) by pouring said aqueous reaction medium, after complete removal of the compound of formula (III), in 2-propanol thus directly precipitating crude cysteamine bitartrate, or the cysteamine salt of c) is cysteamine hydrochloride, or the pH of the aqueous medium of c) is between 12 and 14, or the compound of formula R1-CO—R2 (III) in d) is acetone, or the reaction of d) is carried out at a temperature not higher than 25° C., or the crude thiazolidine (II) obtained in d) is used in the preparation of crude cysteamine bitartrate in a).

6. The process of claim 5 wherein in the thiazolidine of formula (II) R1=R2=methyl, the thiazolidine of formula (II) and the L(+) tartaric acid are reacted in a) in a molar ratio from 1:1 to 1:1.5, the thiazolidine of formula (II) and the L(+) tartaric acid are reacted in a) at a temperature from 45° C. to 55° C., the crude cysteamine bitartrate is isolated from the aqueous reaction medium from a) by pouring said aqueous reaction medium, after complete removal of the compound of formula (III) by distillation, in 2-propanol thus directly precipitating crude cysteamine bitartrate, the cysteamine salt of step d) is cysteamine hydrochloride, the pH of the aqueous medium in c) is between 12.5 and 13.5, the compound of formula R1-CO—R2 (III) in d) is acetone, the reaction in d) is carried out at a temperature not higher than 25° C., and the crude thiazolidine (II) obtained in d) is used in the preparation of crude cysteamine bitartrate in a).

7. A process for purifying crude cysteamine bitartrate, comprising:

h1) preparing a solution of crude cysteamine bitartrate (I) in water h2) pouring said water solution of crude cysteamine bitartrate (I) into 2-propanol, thus precipitating crystalline cysteamine bitartrate (I) from the admixture, h3) isolating crystalline cysteamine bitartrate (I) from the crystallization medium and, optionally, i) drying the isolated crystalline cysteamine bitartrate (I), to obtain pure cysteamine bitartrate (I).

8. A process for the preparation of crystalline anhydrous cysteamine bitartrate (I) polymorph L2 comprising:

1) contacting a cysteamine salt with a base in an aqueous medium at a pH of not less than 10.5, to obtain cysteamine free base of formula (I-B)

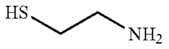

(I-B)

2) reacting in one-pot the cysteamine free base (I-B), in the same aqueous medium, with a compound of formula (III)

R1-CO—R2 (III)

in which R1 and R2 are each independently selected from H, linear or branched $C_1$-$C_{20}$ alkyl, optionally substituted $C_6$-$C_{20}$ aryl and optionally substituted heteroaryl, to obtain a crude thiazolidine of formula (II)

(II)

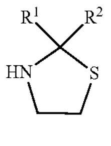

in which R1 and R2 have the meanings reported above, 3) reacting the crude thiazolidine (II) with L(+)-tartaric acid in an aqueous medium, to obtain crude cysteamine bitartrate of formula (I)

(I)

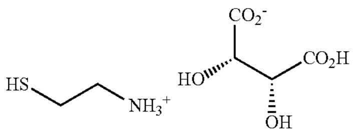

4) precipitating the crude cysteamine bitartrate (I) from the aqueous medium from 3) by pouring it into 2-propanol optionally in admixture with water and then c) isolating the precipitated crude wet cysteamine bitartrate (I) from the aqueous medium, 5) preparing a solution of said crude wet cysteamine bitartrate (I) in water, 6) pouring said water solution of crude cysteamine bitartrate (I) into 2-propanol optionally in admixture with water thus precipitating crystalline cysteamine bitartrate (I), 7) isolating said crystalline cysteamine bitartrate (I) from the crystallization medium and 8) drying the isolated crystalline cysteamine bitartrate (I) up to a water content lower than 1.0% ww, measured by Karl-Fischer method, to obtain crystalline anhydrous cysteamine bitartrate (I) polymorph L2.

9. A process for the preparation of crystalline anhydrous cysteamine bitartrate (I) polymorph L2 comprising:

1) preparing a solution of cysteamine bitartrate (I) in water, 2) pouring said water solution of cysteamine bitartrate (I) into 2-propanol optionally in admixture with water thus precipitating crystalline cysteamine bitartrate (I) from the admixture, 3) isolating crystalline Cysteamine Bitartrate (I) from the crystallization medium, and, 4) drying the isolated crystalline cysteamine bitartrate (I), up to a water content lower than 1.0% ww, measured by Karl-Fischer method, to obtain crystalline anhydrous cysteamine bitartrate (I) polymorph L2.

10. The process of claim 8, wherein in 1) the concentration of cysteamine bitartrate (I) in the water solution, is from 1100 to 500 g/l, or in 1) cysteamine bitartrate (I) is dissolved in water by heating at a temperature not higher than 60° C., or in 2) the volume ratio of 2-propanol and water in the admixture is from 20:1 to 2:1, or in 2) the solution of cysteamine bitartrate in water is poured into 2-propanol under stirring, or in 2) precipitating crystalline cysteamine bitartrate (I) from the admixture is carried out by seeding the admixture with crystals of crystalline anhydrous cysteamine bitartrate (I) polymorph L2, or in 2) precipitating crystalline cysteamine bitartrate (I) from the admixture is carried out by cooling to a temperature between 15 and 30° C.

11. The process of claim 8, wherein in 1) the concentration of cysteamine bitartrate (I) in the water solution, is from 1100 to 500 g/l or from 500 to 440 g/Kg, in 2) the volume ratio of 2-propanol and water in the admixture from 11:1 to 3.0:1, in 2) the solution of cysteamine bitartrate in water is poured into 2-propanol under stirring, and in 2) precipitating crystalline cysteamine bitartrate (I) from the admixture is carried out by seeding the admixture with crystals of crystalline anhydrous cysteamine bitartrate (I) polymorph L2.

12. A process for the preparation of crystalline monohydrate cysteamine bitartrate (I) polymorph L1 comprising:

1) contacting a cysteamine salt with a base in an aqueous medium at a pH of not less than 10.5, to obtain cysteamine free base of formula (I-B)

(I-B)

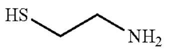

2) reacting one-pot the cysteamine free base (I-B), in the same aqueous medium, with a compound of formula (III)

R1-CO—R2 (III)

in which R1 and R2 are each independently selected from H, linear or branched $C_1$-$C_{20}$ alkyl, optionally substituted $C_6$-$C_{20}$ aryl, and optionally substituted heteroaryl, to obtain a crude thiazolidine of formula (II)

(II)

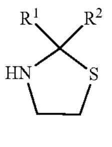

in which R1 and R2 have the meanings reported above, 3) reacting the crude thiazolidine (II) with L(+)-tartaric acid in an aqueous medium, to obtain crude cysteamine bitartrate of formula (I)

(I)

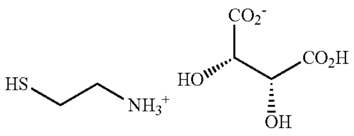

4) precipitating the crude cysteamine bitartrate (I) from the aqueous medium from 3) by pouring it into 2-propanol and then c) isolating the precipitated crude wet cysteamine bitartrate (I) from the aqueous medium, 5) preparing a solution of said crude wet cysteamine bitartrate (I) in water, 6) pouring said solution of crude cysteamine bitartrate (I) in water into 2-propanol thus precipitating crystalline cysteamine bitartrate (I), 7) isolating said crystalline cysteamine bitartrate (I) from the crystallization medium and 8) drying the isolated crystalline cysteamine bitartrate (I) up to a water content from 7.0% to 8.0% ww, measured by Karl-Fischer method, to obtain crystalline monohydrate cysteamine bitartrate (I) polymorph L1.

13. A process for the preparation of crystalline monohydrate cysteamine bitartrate (I) polymorph L1 comprising:

1) preparing a solution of cysteamine bitartrate (I) in water, 2) pouring said water solution of cysteamine bitartrate (I) into 2-propanol optionally in admixture with water thus precipitating crystalline cysteamine bitartrate (I) from the admixture, 3) isolating crystalline cysteamine bitartrate (I) from the crystallization medium, and, 4) drying the isolated crystalline cysteamine bitartrate (I), up to a water content from 7.0% to 8.0% ww, measured by Karl-Fischer method, to obtain crystalline monohydrate cysteamine bitartrate (I) polymorph L1.

14. A process according to claim 1, wherein one or more steps are carried out under inert atmosphere or in the presence of at least an antioxidant agent.

15. A process for converting crystalline monohydrate cysteamine bitartrate (I) polymorph L1 into crystalline anhydrous cysteamine bitartrate (I) polymorph L2 that comprises heating crystalline monohydrate cysteamine bitartrate (I) polymorph L1 at a temperature of at least 45° C. and at a pressure lower than 200 mbar up to a water content lower than 1.0% ww measured by Karl-Fischer method.

16. The process according to claim 8, wherein in 8) a temperature is at least 50° C., and a pressure is lower than 100 mbar.

17. A crystalline anhydrous cysteamine bitartrate polymorph L2 obtainable according to the process of claim 9.

18. A crystalline anhydrous cysteamine bitartrate (I) polymorph L2 powder, said powder being characterized by a water content lower than 1.0%, measured by Karl-Fischer method, a volumetric particle size distribution (PSD), without micronization and after a pre-sieving with a sieve with openings of 600 microns, characterized by D50 not greater than 150 microns and D90 not greater than 250 microns, a bulk density from 0.28 g/ml to 0.35 g/ml, measured according to Ph. Eur. 2.9.34, a tapped density from 0.40 g/ml to 0.43 g/ml, measured according to Ph. Eur. 2.9.34 and/or a Hausner ratio from 1.30 to 1.55.

19. A one-pot process for manufacturing a thiazolidine of formula (II)

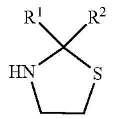

(II)

in which R1 and R2 are independently selected from H, linear or branched $C_1$-$C_{20}$ alkyl, optionally substituted $C_6$-$C_{20}$ aryl, and optionally substituted heteroaryl that comprises:

1) contacting a cysteamine salt with a base in an aqueous medium at a pH of not less than 10.5, to obtain cysteamine free base of formula (I-B)

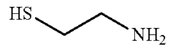

(I-B)

2) reacting in one-pot the cysteamine free base (I-B), in the same aqueous medium, with a compound of formula (III)

R1-CO—R2 (III)

in which R1 and R2 have the meanings reported above, thus providing the crude thiazolidine (II) and, optionally, 3) purifying the thiazolidine of formula (II).

20. The process according to claim 15, which comprises heating crystalline monohydrate cysteamine bitartrate (I) polymorph L1 at a temperature of at least 50° C. and a pressure lower than 100 mbar.

21. The process of claim 1 wherein the pH of the aqueous medium in c) is not less than 12.5.

22. The process of claim 9, wherein in 1) the concentration of cysteamine bitartrate (I) in the water solution, is from 1100 to 500 g/l, or in 1) cysteamine bitartrate (I) is dissolved in water by heating at a temperature not higher than 60° C., or in 2) the volume ratio of 2-propanol and water in the admixture is from 20:1 to 2:1, or in 2) the solution of cysteamine bitartrate in water is poured into 2-propanol under stirring, or in 2) precipitating crystalline cysteamine bitartrate (I) from the admixture is carried out by seeding the admixture with crystals of crystalline anhydrous cysteamine bitartrate (I) polymorph L2, or in 2) precipitating crystalline cysteamine bitartrate (I) from the admixture is carried out by cooling to a temperature between 15 and 30° C.

23. The process according to claim 9, wherein in 4) a temperature is at least 50° C., and a pressure is lower than 100 mbar.

24. The process of claim 19 wherein the pH of the aqueous medium in 1) is not less than 12.5.

* * * * *